United States Patent
Casal-Dujat et al.

(10) Patent No.: US 11,179,483 B2
(45) Date of Patent: Nov. 23, 2021

(54) PER-ORAL NEGATIVE CONTRAST AGENT FOR ABDOMINAL CT

(71) Applicant: LUMENT AB, Lund (SE)

(72) Inventors: Lucia Casal-Dujat, Lund (SE); Olof Öök, Lund (SE); Ingvar Adnerhill, Limhamn (SE); Rickard Öste, Lund (SE); Thomas Fork, Malmö (SE)

(73) Assignee: LUMENTAB, Lund (SE)

( * ) Notice: Subject to any disclaimer, the term of this patent is extended or adjusted under 35 U.S.C. 154(b) by 42 days.

(21) Appl. No.: 16/489,063

(22) PCT Filed: Feb. 26, 2018

(86) PCT No.: PCT/EP2018/054687
§ 371 (c)(1),
(2) Date: Aug. 27, 2019

(87) PCT Pub. No.: WO2018/158195
PCT Pub. Date: Sep. 7, 2018

(65) Prior Publication Data
US 2020/0000942 A1  Jan. 2, 2020

(30) Foreign Application Priority Data
Feb. 28, 2017 (SE) .................................. 1750216-2

(51) Int. Cl.
| | | |
|---|---|---|
| A61B 5/055 | (2006.01) | |
| A61K 49/04 | (2006.01) | |
| A61K 49/18 | (2006.01) | |
| A61K 49/22 | (2006.01) | |

(52) U.S. Cl.
CPC ...... *A61K 49/0461* (2013.01); *A61K 49/0495* (2013.01); *A61K 49/1806* (2013.01); *A61K 49/226* (2013.01)

(58) Field of Classification Search
None
See application file for complete search history.

(56) References Cited

U.S. PATENT DOCUMENTS

| | | | |
|---|---|---|---|
| 8,747,812 B2 | 6/2014 | Wei | |
| 2004/0151756 A1 | 8/2004 | Richards et al. | |
| 2007/0065555 A1* | 3/2007 | Soane | A23L 29/27 426/564 |
| 2007/0065557 A1* | 3/2007 | Pandey | A23L 29/25 426/572 |

FOREIGN PATENT DOCUMENTS

| | | |
|---|---|---|
| CN | 100400105 C | 12/2006 |
| EP | 2050470 A1 | 4/2009 |
| EP | 2662074 A1 | 11/2013 |
| JP | 199589877 A | 4/1995 |
| JP | 5174011 B2 | 4/2013 |
| KR | 101485501 B1 | 1/2015 |
| KR | 1020150005333 A | 1/2015 |
| WO | 1995024184 | 9/1995 |
| WO | 199532005 A1 | 11/1995 |
| WO | 199532006 A1 | 11/1995 |
| WO | 2008046729 | 4/2008 |
| WO | 2014053370 A1 | 4/2014 |
| WO | 2016032346 | 3/2016 |

OTHER PUBLICATIONS

QAQC LAB Consistometer User Guide Contents Jan. 4, 2002, p. 1-3.*
Xie Y R et al, "Effect of Xanthan Gum on Enhancing the Foaming Properties of Soy Protein Isolate," Journal of the American Oil Chemists' Society (Jaocs), Springer, DE, vol. 75, No. 6, Jun. 1, 1998.
Wei, X. et al, "A novel foam fluid negative contrast medium for clear visualization of the colon wall in CT imaging," In: Contrast Media Molecular Imaging, 2011, vol. 6, No. 6, pp. 465-473.; sections 2.1, 2.2, Fig. 1-2.
Schor, M., et al, "The Diverse Structures and Functions of Surfactant Proteins" In: Trends Biochem Sci, Jul. 2014, vol. 41, No. 7. pp. 610-620.
Bamforth, "The Foaming Properties of Beer," J. Inst. Brew, Nov.-Dec. 1985, vol. 91, pp. 370-383.
Perona, Paolo, ETH Zurich, Institute of Hydromechanics and Water Resources Management, Wolfgang Pauli Strasse 15, 8093 Zurich, Switzerland, Appl. Rheol. 15 (2005)218-229.
K. Lomakina and K Míková, "A Study of the Factors Affecting the Foaming Properties of Egg White", a Review, Czech J. Food Sci., vol. 24, No. 3: 110-118.
Ana Cláudia Carraro Alleoni, "Albumen Protein and Functional Properties of Gelation and Foaming," Sci., Agric. (Piracicaba, Braz.) v.63, n.3, p. 291-298, May/Jun. 2006.
Ptaszek et al, "The effect of pectins and xanthan gum on physicochemical properties of egg white protein foams," Journal of Food Engineering 144 (2015) 129-137.
Sumritjate, Benjamas, "Foaming properties of egg albumen as influenced by enzymatic modifications, xanthan gum and some extrinsic factors," 2015 Thesis Report.
International Search Report and Written Opinion for PCT/EP2018/054687 dated May 22, 2018.
Swedish Search Report for priority patent application SE 1750216-2 dated Aug. 29, 2017.

* cited by examiner

*Primary Examiner* — Michael G. Hartley
*Assistant Examiner* — Melissa J Perreira
(74) *Attorney, Agent, or Firm* — Renner, Otto, Boisselle & Sklar, LLP

(57) ABSTRACT

An edible negative contrast agent for CT imaging of the gastrointestinal tract intended for oral intake. The contrast agent is a fluid, aqueous foam displaying a CT density contrast value in the range −300 to −800 HU and having a consistency of 7 to 12 cm as measured with Bostwick consistometer. The contrast agent comprises an aqueous continuous liquid phase having a pH of 6.5 to 8.0 and gas bubbles dispersed in the continuous aqueous liquid phase. The aqueous continuous liquid phase comprises a surfactant, the surfactant being a protein, a hydrocolloid acting as foam stabilizer, a buffering agent, and water.

17 Claims, 5 Drawing Sheets

PER-ORAL NEGATIVE CONTRAST AGENT FOR ABDOMINAL CT

This application is a national phase of International Application No. PCT/EP2018/054687 filed Feb. 26, 2018 and published in the English language, which claims priority to Swedish Application No. 1750216-2 filed Feb. 28, 2017, both of which are hereby incorporated by reference.

FIELD OF THE INVENTION

The present invention relates to a contrast agent for CT imaging. Furthermore, the invention relates to the use of such contrast agent in CT imaging of the small intestine in a subject.

BACKGROUND

Computerized tomography (CT) is a diagnostic imaging technique that creates detailed images of a body, e.g. a human body, with its interior by combining series of X-ray captions that create cross-sectional images or slices of parenchymal organs, muscles, fat tissue, bones, vessels, lymph nodules, etc. in health and disease. Today CT is a frequently used tool due to its lower cost and notably faster examinations compared to other tomography techniques such as magnetic resonance tomography, and also due to its higher availability worldwide. In addition to its common use in diagnosing cancer, CT is widely used to facilitate diagnosing a variety of other diseases and disorders, such as inflammatory diseases, trauma, anomalies, etc.

In CT of the abdomen (CT-abd), contrast agents are used for demarcating structures by increasing differences in density between tissue compartments. The enhanced difference in contrast improves visualization of details necessary for the radiologist to detect and follow abnormalities within the abdomen and pelvis over time and thus, with a possible medical diagnosis. The radiodensity of structures and/or materials is measured in Hounsfield Units (HU). The reference points are defined by solid metal, air, and water that have radiodensity values of +1000 HU, −1000 HU and 0 HU, respectively, and independently of the tube voltage used. CT scan images are observed in grey scale (cf. FIG. 1). The abdominal organs and structures are displayed in a variety of colors in the grey scale depending on the radiodensity of their composition, from white (such as bones; around +1000 HU), to light grey (such as blood vessels; around +70 HU), and black (such as air in the lungs; around −1000 HU).

A patient routinely referred to CT-abd is usually prepared with a per-oral agent for demarcating the gastro-intestinal tract. Up until now, the most commonly used demarcating agent has been a diluted solution of an iodine contrast medium meant for intra-venous application, resulting in a white bowel content, i.e. with positive HU. Other agents are iso-osmotic solutions that provide densities of around 10 HU, exhibiting bowel lumen in grey, close to the color of other body structures. Thus, positive oral filling agents provide no or unsatisfactory contrast between the bowel wall and the lumen of the small intestine on CT images. As a consequence, images of the bowel wall are less easy to read which may result in radiological diagnoses of reduced quality, including both false positive and negative diagnoses.

Consequently, an increasing number of patients—especially younger patients with small bowel diseases—are today examined with magnetic resonance enterography (MRE) of the small bowel. MRE provides outstanding images because the small bowel wall and mucosa present in white nuances, i.e. with high signals, whereas the bowel lumen is shown in black on T1-sequences, i.e. in low or no signals. The large step in signals greatly improves diagnostics of the small bowel wall and mucosa. However, the major disadvantages of MRE are protracted time of examination, long periods of holding the breath, and restricted accessibility of MR-machines. Thus, CT-abd will remain the first imaging method of choice in most cases for the foreseeable future.

Hence, there is an interest and need for a negative, "black" filling, contrast agent, which would provide notably larger contrast against the mucosal lining and of the gut wall, thereby creating an opportunity for improved medical evaluation. The lower the luminal contrast density value, the larger the contrast difference, the better image display of the mucosa and bowel wall and the higher the possibility to perform 3D presentation that is virtual endoscopy. It should however be noted that a too large contrast (i.e. density contrast values close to −1000 HU) obscures the interface through so called "hard beam artifacts". Air might be used as a black bowel filling, contrast agent. However air has to be insufflated through a naso-gastric tube. Insufflated air is unpleasant, tube placement is painful and luminal air gives rise to hard beam artifacts. Given its localization downstream the stomach and duodenum and upstream the colon, the small intestine is not easy to access and manipulate.

In the art, attempts to address the clinical urge for a negative bowel filling agent have been made, but so far, no such agent is commercially available.

In CA 1116084, dating back in 1982, a system for inflating the stomach of a patient to enable double-contrast barium meal radiography is disclosed. The system comprises two liquid formulations to be swallowed sequentially. The first formulation is a non-toxic alkaline solution or dispersion of a carbonate or bicarbonate which may be colored, flavored and thickened. The second formulation comprises a solution of a food grade acid. The system is intended to provide for in situ gas generation. Although being a potential interesting system for demarcating the small intestine, the disclosed technique suffers from proving uneven distribution of the contrast agent. Further, the control over the contrast (i.e. radio density values) is limited.

In CN1233505 compositions based on vegetable oils for use as negative contrast agents for clinical use in abdominal CT are disclosed. Although being suitable for demarcation of the small intestine and providing fairly even distribution, these contrast media suffer from not providing sufficiently negative density values.

Rectal insufflation for demarcation of the colon for CT-scan examination is a well-stablished technique for virtual 3D rendering of the large bowel in CT-colonography that provides a great leap in density between wall and lumen, though the generated contrast is too low. Such a direct access to the small bowel does not exist. In a paper in *Contrast media and molecular imaging* (vol. 6, p. 465-473, 2011) a novel foam fluid negative contrast medium for clear visualization of the colon wall in CT imaging is disclosed (cf. also WO 2007/131390). The negative contrast is intended as an enema for rectal administration for colon visualization in CT-scan examination for diagnosis of colon. It provides density contrast values of down to −120 HU. A contrast of −120 HU, reported to be sufficient for detecting polyps (≥2 mm) in the colon, is however not considered sufficiently low for rendering 3D, virtual images of small bowel loops.

Thus, there is a need in the art for a negative contrast agent providing values of low density suitable for demarcating the small bowel, offering improved diagnostic value for the patient and doctor.

SUMMARY

Consequently, the present invention seeks to mitigate, alleviate, eliminate or circumvent one or more of the above identified deficiencies and disadvantages in the art singly or in any combination by providing an edible negative contrast agent for CT imaging of the gastrointestinal tract intended for oral intake, the contrast agent being a fluid, aqueous foam displaying a CT density contrast value in the range −300 to −800 HU and having a consistency of 7 to 12 cm, such as 8.5 to 12.0 cm, as measured with Bostwick consistometer over 30 seconds at 23±1° C. The contrast agent comprises an aqueous continuous liquid phase having a pH of 6.5 to 8.0 and gas bubbles dispersed in the continuous aqueous liquid phase. The aqueous continuous liquid phase comprises a surfactant, the surfactant being a protein, a hydrocolloid acting as foam stabilizer, a buffering agent, and water.

According to an embodiment, the gas bubbles are air bubbles. According to alternative embodiment, the gas bubbles are bubbles of $CO_2$, $N_2$, $N_2O$ and/or argon, such as of $N_2$, $N_2O$ and/or argon.

The weight ratio surfactant:hydrocolloid in the continuous liquid phase may be from 8:1 to 2:1, from 3:1 to 5:1, or from 7:2 to 9:2. According to an embodiment, the surfactant comprises ovalbumin. Further, the hydrocolloid may be selected from the following groups:
  polysaccharides, such as starch based polysaccharides (e.g. arrowroot, cornstarch, katakuri starch, potato starch, sago, or tapioca);
  natural gums (e.g. alginin, gum Arabic, guar gum, locust bean gum, tragacanth, a carrageenan, a pectin, or xanthan gum);
  chitosans; and
  modified natural gums (e.g. propylene glycol alginate).

According to an embodiment, the hydrocolloid is a natural gum or a modified natural gum. Preferably, the natural gum is xanthan gum and/or propylene glycol alginate.

The buffering agent may comprise a monovalent counter-ion. Preferably, such a counter-ion is sodium and/or potassium. In an embodiment wherein the buffering agent is phosphate based and the counter-ions are sodium and potassium, the phosphate concentration in the liquid phase may be between 0.01 and 1 molar. Preferably, the phosphate concentration in the liquid phase in embodiments wherein the buffering agent is phosphate based is between 0.02 and 0.5 molar, such as about 0.05 molar.

According to an embodiment, the edible negative contrast agent comprises at least 35 vol % dispersed air bubbles, such as more than 50 vol % dispersed air bubbles. Thus, the contrast agent may comprise 30 to 70 vol % dispersed air bubbles at 25° C., such as between 35 and 55 vol %, e.g. between 35 and 45 vol %, dispersed air bubbles at 25° C., or between 55 and 65 vol % dispersed air bubbles at 25° C. The contrast agent may display a density contrast value in the range −500 to −700 HU.

According to an exemplary embodiment, the edible, oral negative contrast agent has one or more of the following characteristics:
  a content of dry matter in the continuous aqueous liquid phase of 5 wt % or less, such as 3.0 wt % or less; and/or
  a content of 0.01 to 1.0 wt %, preferably 0.1 to 0.7 wt %, of the hydrocolloid in the continuous aqueous liquid phase; and/or
  a content of 0.1 to 5 wt % of the surfactant, preferably 0.5 to 2.5 wt %, in the continuous aqueous liquid phase; and/or
  a CT density in the range −300 to −700 HU, such as in the range −500 to −700 HU.

According to a further aspect of the invention, there is provided an aqueous liquid composition for providing the contrast agent. The composition of the aqueous liquid composition corresponds to the one of the continuous aqueous liquid phase.

According to another aspect of the invention, there is provided a dry composition for providing the aqueous liquid composition for providing the contrast agent. The dry composition comprises a surfactant, the surfactant being a protein, a hydrocolloid, and a buffering agent. Preferably, the surfactant comprises ovalbumin. According to an exemplary embodiment, the hydrocolloid is a natural gum, preferably the natural gum being xanthan gum, and the buffering agent is phosphate based, preferably the buffering agent comprising $NaH_2PO_4$ and $K_2HPO_4$. Further, according to such an exemplary embodiment:
  the weight ratio surfactant:hydrocolloid in the dry composition is from 10:1 to 1:1, such 8:1 to 2:1; and/or
  the content of the buffering agent in the dry composition is at least 20 wt %, such as at least 40 wt %; and/or
  the content of the surfactant and the hydrocolloid in the dry composition all in all is at least 35 wt %, such as at least 50 wt %; and/or
  the content of the surfactant, the gelling agent, and the buffering agent in the dry composition all in all is at least 75 wt %, such as at least 85 wt %.

According to another aspect of the invention, there is provided for use of the edible negative contrast agent as contrast agent in CT imaging of the gastrointestinal tract including the small intestine. Similarly, the present edible negative contrast agent may be for use as contrast agent in CT imaging of the gastrointestinal tract including at least the upper part of the small intestine in a subject, e.g. a human being. In such use, the contrast agent may preferably be orally administered to the subject to be examined prior to the CT imaging. Especially, the contrast agent may be for use in demarcation of at least the upper part of the small bowel in abdominal CT imaging.

According to another aspect of the invention, there is provided for the use of the edible negative contrast agent as contrast agent in imaging of the gastrointestinal tract by abdominal MRI or by abdominal ultrasound imaging. Similarly, the present edible negative contrast agent may be for use as contrast agent in imaging of the gastrointestinal tract by abdominal MRI or by abdominal ultrasound imaging in a subject, e.g. a human being. In such use, the contrast agent may preferably be orally administered to the subject to be examined prior to the abdominal MRI or the abdominal ultrasound imaging.

Further advantageous features of the invention are defined in the dependent claims. In addition, advantageous features of the invention are given in the detailed description.

BRIEF DESCRIPTION OF THE DRAWINGS

The above and other aspects, features and advantages of which the invention is capable of will be apparent and elucidated from the following description of the present invention, reference being made to the accompanying drawings, in which FIG. 1. Depicts the Honounsfield Units (HU), and the grey scale at which structures are displayed in CT-scan images.

DETAILED DESCRIPTION

Figure 1:
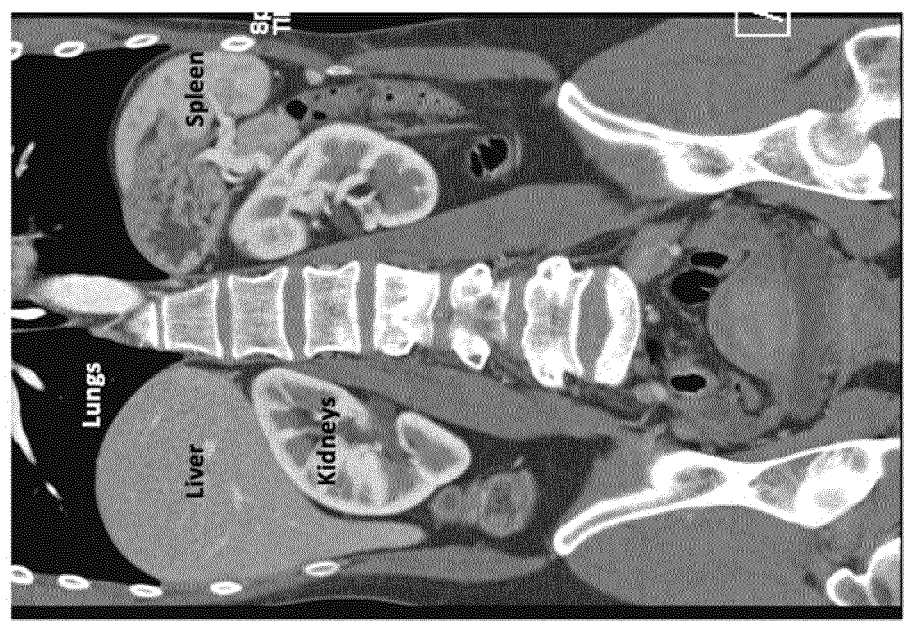
Figure 1:
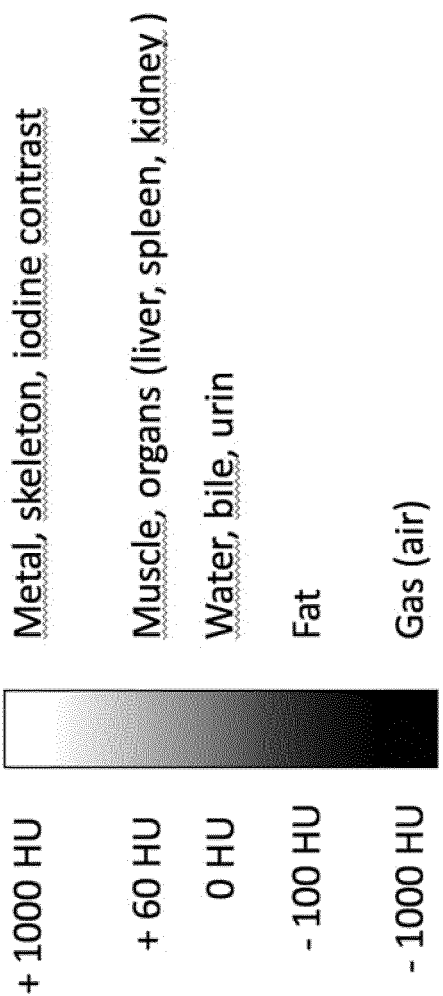

Systems composed of air dispersion in aqueous media provide negative density contrast values in the range of −1000 HU to 0 HU, depending on the proportion of dispersed air, and may thus be used as negative contrast agents. For abdominal CT imaging, the negative density contrast values provided should preferably be in the range −300 to −800 HU corresponding to a fairly high volume proportion of air. Further, a contrast agent for use in CT imaging should be sufficiently stable in the gastrointestinal tract to provide essentially the same CT negative density contrast values throughout the gastrointestinal tract.

As recognized in the art, dispersion of air in liquids, i.e. foams, may be provided by whipping or beating an aqueous solution or dispersion, comprising a foaming agent. Typical examples of foaming agents are detergents. The type and amount of the foaming agents will affect properties of the final foam. Further, also the amount of air incorporated into the aqueous solution or dispersion will influence in the properties of the final foam.

Surfactants are extensively used together with thickeners or stabilizers, e.g. a hydrocolloid, to provide and stabilize foams consisting of air bubbles dispersed in aqueous phase. Mechanisms of stabilization of the thickeners or stabilizers are based on promoting electrostatic and/or steric repulsion, and/or increasing the viscosity of the continuous aqueous phase between the bubbles. They will thus inherently also affect the viscosity and consistency of the final foam (i.e. the aqueous dispersions of air). Furthermore, also the volume ratio of dispersed air, which is the factor that determines the degree of negative density of the contrast agent, will affect the viscosity and consistency of the final foam. Thus, it has been shown to be difficult to provide a bowel filling stable negative contrast agent with not only low enough negative contrast values (i.e. −300 or lower such as between −500 and −800 HU), with optimal image quality and stability, but also with an acceptable consistency for oral intake.

It has been found that a negative contrast agent for CT imaging of the small bowel may be provided by dispersing a gas, such as air, in an aqueous composition comprising a surfactant and stabilizer. Further, also other gases, e.g. $CO_2$, $N_2$, $N_2O$, and argon, may be dispersed in an aqueous composition comprising a surfactant and stabilizer to provide a negative contrast agent for CT imaging of the small bowel. Of these alternative gases, $N_2$, $N_2O$, and argon are preferred.

High molecular weight molecules, such as proteins, are common food-based surfactants used in products with good foamability and foam stability. High molecular weight surfactants, such as proteins, allow the formation of thicker and more stable films between bubbles in the foam system compared to surfactants of low molecular weight despite the last ones diffuse much faster and decrease the surface tension more effectively than high molecular weight molecules. However, even though molecules such proteins diffuse slower they are able to form a confinement and aggregation of molecules even before adsorbing at the air-water interface, and thus create thicker and more stable films.

Among the food-based proteins, egg white protein has been found to have exceptional functional properties on gelation and foam formation. Egg white protein, or egg albumen, is comprised by several globular proteins (ovalbumin, ovotransferin, ovomucoid, ovomucin, lysozyme, globulin, avidin). Even though ovalbumin is one of the critical proteins, the combination of different proteins contained in egg albumen is advantageous in foaming and foam stability properties. A mixture of opposed charges and the formation of intermolecular bonds improve the stabilization of food foams. The mixture may thus preferably comprise at least ovalbumin, ovomucin and ovoglobulin.

In the dispersion, the surfactant, e.g. egg albumen, permits the formation of air bubbles and stabilization thereof, due to their amphiphilic nature. Albumen proteins turned out to have exceptional functional properties on foam formation and gelation and here hence preferred. However, in order to enhance the stabilization of the dispersed air bubbles, a foam stabilizer, e.g. a hydrocolloid acting as foam stabilizer, such as natural gum should be present in the liquid composition.

Figure 2A:
In FIG. 2a the abdominal window being the window used for diagnosis and exhibiting the lumen of the gut in dark is depicted.
Figure 2B:
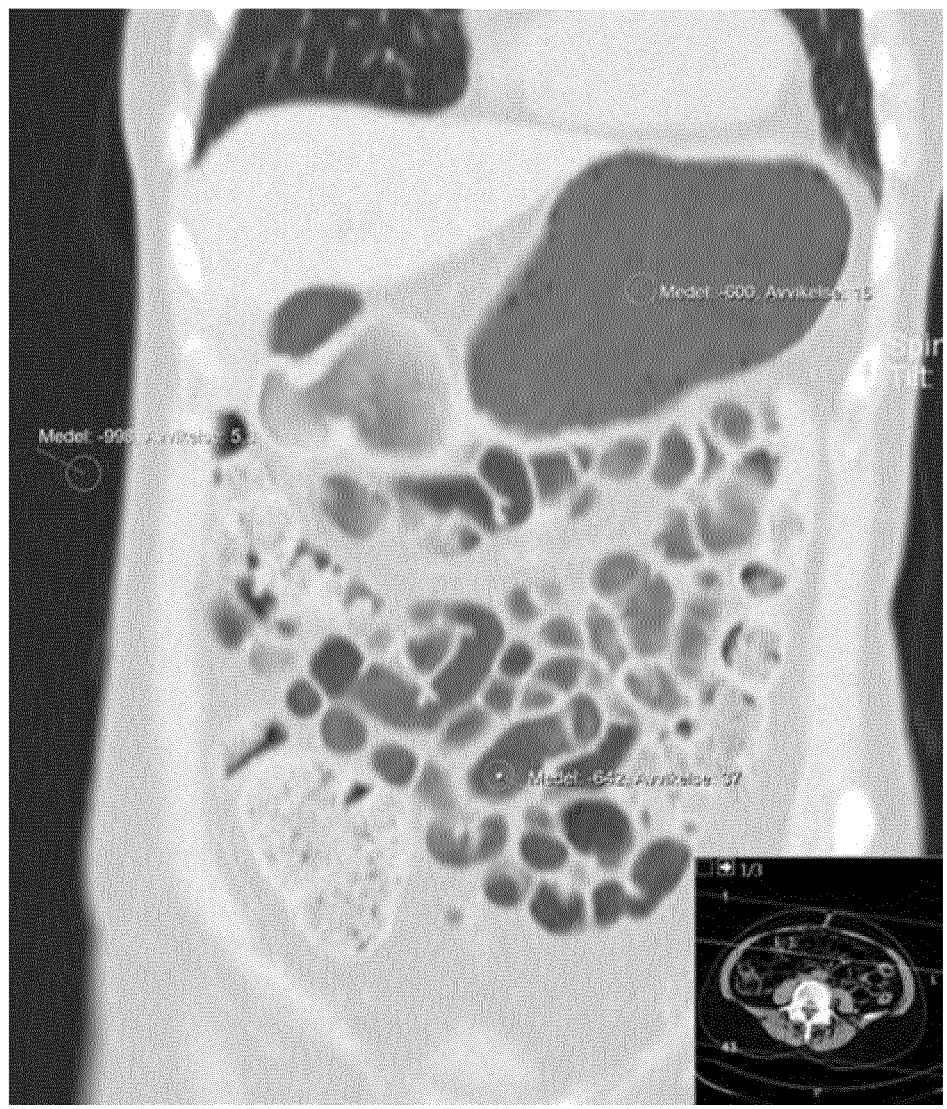
in FIG. 2b the lung window showing the homogeneity of the foam and the presence of endogenous air in the subject's gut is depicted; and in FIG. 2c an inverted image showing the negative contrast agent in white is depicted.
Figure 2C:
FIG. 2 Depicts images obtained from abdominal CT-scan examinations in a healthy subject by use of the present contrast agent according to one embodiment having a density contrast around minus 600 HU.

Presence of a surfactant, being a protein, and hydrocolloid acting as foam stabilizer in proper ratios, in the liquid composition allowed for providing a negative contrast agent displaying a CT density contrast value in the range −300 to −800 HU, still being fluid and sufficiently stable. In order to maintain the functional properties of the egg albumen and the protein network stable not only during the foam preparation and storage but also during its intake, the pH of the contrast agent should be stable and within a range of 6.5 to 8.0. Thus, a buffering agent was used in order to achieve the optimal and stable pH conditions that would provide the protein a suitable and optimal environment to be stable and to enhance the foamability and foam stability not only under storage but also under the harsh gastrointestinal conditions. Further, it was found that adding a buffering agent to the liquid composition did not affect the foaming properties. Inclusion of a buffering agent was deemed to be essential for providing a negative contrast agent for CT imaging for oral intake, in order for the contrast agent to remain stable upon gastric transit to the small intestine. Actually, the buffering agent was further found to stabilize the foam also at less and harsh conditions and provide longer shelf life. Indeed, it was found that the negative contrast agent allowed for CT imaging of the small intestine after oral intake of the present negative contrast agent (cf. FIGS. 2a-c).

An embodiment, thus relates to an edible negative contrast agent for CT imaging of the intestines intended for oral intake. The negative contrast agent is a fluid aqueous foam displaying a CT density contrast value in the range −300 to −800 HU, preferably in the range −550 to −700 HU. The contrast agent comprises a continuous aqueous liquid phase comprising a surfactant, the surfactant being a protein, a hydrocolloid acting as foam stabilizer, a buffering agent, and water. The continuous liquid phase has a pH of 6.5 to 8.0, e.g. about 7.3. Further, the contrast agent comprises gas bubbles, preferably air bubbles, dispersed in the continuous aqueous liquid phase. According to an alternative embodiment, the gas bubbles in the contrast agent are bubbles of $CO_2$, $N_2$, $N_2O$, or argon, such as $N_2$, $N_2O$, or argon, dispersed in the continuous aqueous liquid phase The contrast agent preferably comprises at least 35 vol. % dispersed gas bubbles (e.g. air bubbles), such as more than 50 vol % dispersed gas bubbles, at 25° C. According to an embodiment, the contrast agent comprises 30 to 70 vol % dispersed gas bubbles (e.g. air bubbles) at 25° C., such as between 35 and 55 vol %, e.g. between 40 and 45 vol %, dispersed gas bubbles (e.g. air bubbles) at 25° C., or between 55 and 65 vol % dispersed gas bubbles (e.g. air bubbles) at 25° C. A higher proportion of dispersed gas (e.g. between 55 and 65 vol % dispersed gas bubbles at 25° C.), provides lower contrast values (cf. around −600 HU) and requires lower amount of surfactant and foam stabilizer to provide stable foams. A somewhat lower higher proportion of dispersed gas (e.g. between 35 and 55 vol %, or between 40 and 45 vol %, dispersed gas bubbles at 25° C.), may provide enhanced bowel distention due to the higher water content, thereby potentially improving the diagnosis by making visible spaces hidden in loops of the bowel. A somewhat lower higher proportion of dispersed gas however requires somewhat more surfactant and foam stabilizer to provide stable foams.

In order to be useful in demarcating the small bowel and to be patient friendly, it was deemed necessary that the contrast agent is administered orally to reach the small bowel via gastric transit, instead of retrograde filling via rectum or antegrade through a naso-gastric tube. Further, fairly large volumes of the contrast agent, such as about 0.9 to 1.2 L, were deemed to be required to fill up the small intestine. By providing a negative contrast agent being liquid-like and fluid, but still sufficiently stable, the contrast agent may be drunk by the subject, e.g. a human being, to be examined. It was found that the consistency, being related to the viscosity, of the contrast agent was important for the drinkability. In order to be drinkable and stable, the contrast agent should have a consistency of 7 to 12 cm, such as 8.5 to 12.0 cm, as measured with a Bostwick consistometer. As recognized by the skilled person, Bostwick consistency is a measure commonly used in the food industry to evaluate the consistency of foodstuff being viscous fluids. In short, Bostwick consistency is determined as the distance covered by a given sample of fluid over a flat slot in a given time interval at constant temperature. As used herein, Bostwick consistency relates to the distance covered at 23±1° C. over 30 seconds for a given sample of fluid. The distance is to be measured by means of a narrow consistometer. A narrow consistometer is a consistometer having a reservoir with b/H-ratio of 1.3 to 1.4, "b" being the width of the reservoir and "H" the height thereof. As an example, a Bostwick Consistometer from CSC Scientific Company Inc. may be used. Further, according to an embodiment, the Bostwick consistency is determined in accordance with ASTM F1080-93 (2013) "*Standard Test Method for Determining the Consistency of Viscous Liquids Using a Consistometer*" with the following modifications:

Step 5.2 was omitted as this step is redundant for the present contrast agent being a homogenous foam; and
The duration of test in Step 5.6 was 30 sec.

A too stiff foam, with thick consistency, e.g. a Bostwick consistency lower than 7 cm, such as lower than 8.5 cm, was found to be harder to consume and resulting in concurrent swallowing of air, not only raising the discomfort of the subject but also resulting in blurred CT-images. Thus, the contrast agent should be sufficiently fluid to be drinkable rather than spoonable. It was further found that especially for foams displaying higher contrast values, i.e. comprising more than 60% dispersed air, it is preferred if the Bostwick consistency is at least 8.5 cm. Foams with up to 60% dispersed air may still be acceptable provided that the Bostwick consistency is at least 7 cm. Further, presence of large air bubbles not evenly dispersed in the contrast agent will result in a spotty bowel filling that would interfere in the CT impairing radiologic diagnosis. Typically, at least 80%, such as at least 90%, of the bubbles have a size of less than 200 µm, such as less than 150 µm. According to some embodiments, at least 80% of the bubbles have a size of less than 100 µm, such as less than 80 µm.

The surfactant may be egg albumen, as egg albumen provides good foaming properties to aqueous solutions. Further, egg albumen is an edible, well-accepted food additive. Apart from egg protein allergy, its use has in principle no contra indications. The major foaming component in egg albumen is ovalbumin. According to an embodiment, the surfactant comprises ovalbumin. While ovalbumin may be used alone as surfactant, it is preferred to use a mixture of proteins at least comprising at least ovalbumin, ovomucin, and ovoglobulin. Preferably, the surfactant is egg albumen. The egg albumen may be egg albumen powder, such as regular, high gel instant, super high gel instant, or high whip instant egg albumen powder. Preferably, the egg albumen powder is high gel instant egg albumen powder.

Further, the protein surfactant may be enzymatically treated to improve the foamability and foam stability properties by hydrolyzing the protein—and consequently reducing the molecular weight of the protein, increasing the number of ionizable groups, exposing hydrophobic aminoacids, and exposing functional groups that enhance intermolecular interactions.

Various hydrocolloids may be used to stabilize the continuous liquid phase of the contrast agent, by increasing the viscosity thereof. As recognized by the skilled person, hydrocolloids are typically hydrophilic polymers of vegetable, animal, microbial or synthetic origin that contain many hydroxyl groups. Hydrocolloids may be polyelectrolytes. The hydrocolloid in the present contrast agent may thus be:

a polysaccharide, such as a starch based polysaccharide (e.g. arrowroot, cornstarch, katakuri starch, potato starch, sago, or tapioca);
a natural gum (e.g. agar, alginic acid, gum Arabic, guar gum, locust bean gum, tragacanthpropylene glycol alginate, a carrageenan, a pectin, or xanthan gum);
chitosan; or
a modified natural gum (e.g. propylene glycol alginate).

In a preferred embodiment, the hydrocolloid is a natural gum, such as xanthan gum, alginic acid, or a pectin. Xanthan gum, alginic acid, and pectin, comprising carboxylic groups, have the ability to interact with the protein used as surfactant. Further, due to their molecular structure and the presence of electrically charged functional groups, i.e. carboxylates, pectin, alginic acid, and xanthan gum are capable of creating stable systems of a complex nature. Alginic acid may be used in its natural form or as the corresponding carboxylic ester of propylene glycol, i.e. propylene glycol alginate. Preferably, the natural gum is xanthan gum (e.g. E415) and/or propylene glycol alginate (e.g. E405).

The continuous aqueous liquid phase may comprise 0.01 to 1.0 wt % of the hydrocolloid, such as 0.1 to 0.7 wt %, or 0.2 to 0.5 wt %, of the hydrocolloid. It was found that a too low amount of the hydrocolloid not significantly improved the stability of the foam. On the other hand, a too high amount of the hydrocolloid will reduce the flowability of the foam and thus decreases the patients' acceptance during the intake, and even result in non-fluid stiff foam. Further, a too high amount of the hydrocolloid will promote foams with high polydispersity and many big visible bubbles. As further discussed below, not only the absolute amount of the hydrocolloid is important but also the relative amount in relation to the surfactant.

The buffering agent is to maintain the pH of the continuous liquid phase of the contrast agent between 6.5 and 8.0, preferably even along the harsh pH conditions of the gastrointestinal tract. The skilled person is familiar with various suitable buffering agents to be used in orally administered compositions to provide a pH between 6.5 and 8.0. As an example, the buffering agent may be phosphate based, e.g. comprise hydrogen phosphate ($HPO_4^{2-}$) and di-hydrogen phosphate ($H_2PO_4^-$). The buffer may further be carbonate based, e.g. comprise hydrogen carbonate ($HCO_3^-$) and carbonate ($CO_3^{2-}$). As recognized by the skilled person, buffering agent typically comprises counter-ion(s). Phosphate buffers with divalent cations, such as $Ca^{2+}$ and $Mg^{2+}$, are less preferred as such phosphate salt may be poorly soluble. This also applies to carbonate based buffers. Hence, the buffering agent may comprise a monovalent counter-ion, e.g. a cation. Preferably, the counter ion is a monovalent cation. More preferably, the counter-ion is sodium and/or potassium. The buffering agent may thus be a mixture of $KH_2PO_4$ and $Na_2HPO_4$, or a mixture of $K_2HPO_4$ and $NaH_2PO_4$. Using a buffering agent comprising sodium as well as potassium has the advantage of providing a balanced electrolyte intake. For a contrast agent to be taken orally, this is a desired property. Typically, the buffering agent is used in amount corresponding to from 0.01 to 1 molar, such as between 0.02 and 0.5 molar, of the buffering specie (acid and its conjugate base; e.g. $H_2PO_4^-$ and $HPO_4^{2-}$). Thus, the phosphate concentration (i.e. the accumulative concentration of $H_3PO_4$, $H_2PO_4^-$, $HPO_4^{2-}$, and $PO_4^{3-}$), if the buffering agent is phosphate based, in the continuous liquid phase may be between 0.01 and 1 molar, such as between 0.02 and 0.5 molar, or between 0.02 and 0.1 molar. The phosphate concentration in the continuous liquid phase may be about 0.05 molar, or about 0.1 molar. The molar ratio of hydrogen phosphate ($HPO_4^{2-}$) to di-hydrogen phosphate ($H_2PO_4^-$) may vary. As the buffer in the first place is to provide the egg albumen protein the optimal conditions to enhance its functionality, and to maintain a neutral pH during the gastric transit, exposing the contrast agent to acidic conditions, the molar ratio of hydrogen phosphate ($HPO_4^{2-}$) to di-hydrogen phosphate ($H_2PO_4^-$) may be from 1:1 to 1:10, such as from 1:1 to 1:5, or from 1:2 to 1:4. It is of less importance to buffer the contrast agent against alkaline conditions, as the pH of the intestinal fluid is close to the pH of contrast agent.

The overall content of dry matter in the continuous liquid phase will be fairly low, and the continuous liquid phase will mainly consist of water. According to an embodiment, the content of dry matter in the continuous liquid phase is 5 wt % or less, such as 3.0 wt % or less. The content of dry matter in the continuous liquid phase may be at least 0.2 wt %, such as least 0.5 wt % or at least 1.0 wt %.

As already mentioned, the continuous liquid phase may comprise 0.01 to 1.0 wt % of the hydrocolloid, such as 0.1 to 0.7 wt % of the hydrocolloid. Further, the continuous liquid phase may comprise 0.1 to 5 wt % of the surfactant, preferably 0.5 to 2.5 wt % of the surfactant. In order to provide a negative contrast agent that is stable for at least one hour (no or limited drainage as well no or limited increase in polydispersity), the weight ratio surfactant:hydrocolloid in the continuous liquid phase may be from 10:1 to 1:1, such as from 8:1 to 2:1, from 3:1 to 5:1, or from 7:2 till 9:2. Preferably, the weight ratio surfactant:hydrocolloid in the continuous liquid phase exceeds 1:1, i.e. the continuous liquid phase comprises a higher weight proportion of the surfactant than of the hydrocolloid. The weight ratio surfactant:hydrocolloid in the continuous liquid may be about 4:1.

Furthermore, as the contrast agent is intended for oral administration, the continuous liquid phase may comprise 0.1 to 0.4 wt % of a flavoring agent. The flavoring agent serves to make the contrast agent tasty and pleasant to drink. This may be an important feature, as a fairly large amount of the contrast agent is to be consumed prior to the CT examination. As the contrast agent is intended for oral administration, the constituents should be edible. Preferably, the constituents in the liquids phase should even be accepted as food additives and the amount contained should not exceed the upper safe intake. According to an embodiment, at least some of the constituents in the liquids phase, are constituents listed in the European pharmacopeia $9^{th}$ Edition. Even though the consumption of the negative contrast agent is isolated and single, neither daily nor periodic, the components amounts are preferably within the reported and registered safe intake by the pertinent authority.

According to an embodiment, the constituents in the aqueous liquid phase, apart from water, essentially consist (e.g. the content of other constituents being less than 0.1 wt. %, such as less than 0.01 wt. %) of:

egg albumen powder;
xanthan gum and/or propylene glycol alginate; e.g. xanthan gum;
sodium and potassium phosphates; and
optionally flavoring agent(s).

A further embodiment relates to an aqueous liquid composition for providing the present contrast agent. The composition of the liquid composition corresponds to the one of the continuous aqueous liquid phase of the negative contrast agent. Such an aqueous liquid composition may be provided to health care institutions. By whipping (also known as beating) the liquid composition, a ready to use negative contrast agent may be provided at health care institution for use in abdominal CT examinations. The subject to be examined is then to drink the contrast agent shortly before being examined. The subject is to drink it evenly and orderly in 40 to 60 minutes. Preferably, the subject is to take each dose in 10 to 15 minutes, each dose preferably contains 0.3 to 0.4 L of foam. The subject can take the negative contrast agent being sitting down, or standing up, or walking around. Preferably, the subject walks around for at least 20 minutes during the intake to boost peristaltic movements in the gastrointestinal tract and thus, enhance a homogeneous filling and distribution of the foam all along the gut. The negative contrast agent can be drunk directly from the glass, or using a straw, or using a table spoon, as the subject feels more comfortable with. Preferably, the negative contrast agent is drunk directly from the glass to avoid the incorporation of air that has been observed in the cases that the straw or spoon have been used likely due to the partial filling of foam in the mouth and consequently swallow of air. Given that the stability of foams is typically limited, it may be necessary to provide the negative contrast agent by whipping the liquid composition shortly, e.g. within 1 hour, before the foam intake and the corresponding CT examination. Thus, it is may be preferred to provide the aqueous liquid composition for providing the present contrast agent to health care institutions, rather than providing the contrast agent ready to use. As outlined further below, the present contrast agent may also be provided to health care institutions as dry powder to be dispersed and subsequently whipped to provide the present contrast agent. The stability of the negative contrast agent should however be sufficient to provide essentially constant and consistent negative CT density contrast values throughout the small intestine. An important objective of the present invention is to provide a stable, fluid and palatable negative contrast agent with an air content that provides an optimal negative density contrast for clear CT-abd. As discussed herein, stable foams are typically not fluid.

For safety and hygienic reasons, the pre-foam liquid product may be sterilized, e.g. UV-C sterilization. Heat sterilization may however be less preferred, as it may affect the functional properties of the constituents in the liquid composition negative, e.g. denaturizing the protein. Further, the pre-foam liquid product may be stored under an inert gas, such as argon or nitrogen, and chilled (5±3° C.). Furthermore, a preservative, e.g. paraben, may be included in the pre-foam liquid product.

According to an embodiment, there is provided a dry powder for providing the present contrast agent. The powder may be provided by freeze drying, or spray drying, the present aqueous liquid composition used in providing the contrast agent. This may be advantageous, as the freeze dried or spray dried powder is easily dispersed in water and subsequently whipped to provide a stable foam, i.e. the present contrast agent. Further, a powder, e.g. a freeze dried powder, has good shelf life.

Whipping the liquid composition to provide the negative contrast agent may be performed in a two-stage procedure. In a first stage, gas, e.g. air, is incorporated into the liquid composition to provide a composition comprising dispersed gas, e.g. air, bubbles of a significantly wide bubble size distribution. In a second stage, larger bubbles are broken up until obtaining as low polydispersity in bubble size as possible in as homogeneous as possible foam. According an embodiment, at least 80%, such as at least 90%, of the bubbles has a diameter of less than 200 µm. Further, at least 25% of the bubbles may have a diameter of 25 to 150 µm. According to some embodiments, at least 80%, such as at least 90%, of the bubbles has a diameter of 20 to 80 µm. Further, at least 25% of the bubbles may have a diameter of 40 to 60 µm. The percentage of bubbles of various size ranges may be determined by measuring the size for at least 250 bubbles, such as at least 500 bubbles in microscope. The lower polydispersity in bubble size, the more stable the foam is and the clearer CT-image is obtained (big bubbles in small bubbles bulk foam create interferences and patchy CT-images). While it is preferred to reduce the bubble size, a foam comprising of too small bubbles suffers from reduce stability due to the decrease in bubble elasticity resulting from excessive insolubilisation of proteins at the gas-water interface.

The most important indication for a bowel filling contrast agent with negative HU is to improve diagnostics of bowel diseases, such as Crohn's disease. It is well known that any inflammatory lesion will light up after intra-venous injection of an iodine contrast medium. This reaction is quite obvious in big lesions, but doubtful in tiny because the foreseeable difference in contrast between a minute lesion and its surroundings is low, if not absent. If, on the other hand, the HU of abutting tissue compartments and bowel interior is reduced, detection of a small mucosal lesion, hopefully early in disease, is facilitated.

Theoretically, an increase leap in contrast makes tiny and early lesions detectable. That is why a negative bowel filling agent would be recommendable even for CT-examinations of the abdomen in patients who do not suffer a primary bowel disease, because a hitherto silent disease may be disclosed and treatment initiated to the benefit of the patient.

Another indication is for healthy subjects who are enrolled in CT-screening programs for various abdominal diseases. Thus, a negative bowel filling contrast agent as a preparatory treatment prior to CT of the abdomen and small intestine is foreseen to add new and improved radio-diagnostic possibilities, i.e. improved imaging properties offer great diagnostic potentials.

CT-based virtual endoscopy of the small bowel is only possible if the gut content differs greatly in HU from the gut wall. In order to achieve a 3D-rendering, the difference must be 600 HU or more depending on the software used. Virtual enteroscopy is indicated in all patients in whom the referring doctor is considering capsule endoscopy of the small bowel, typically in patients with a gastro-intestinal bleed or an inflammatory disease. Room occupying lesions, be it inflammatory in origin or a bleeding that rather often emanates from a bowel tumor, such as a carcinoid, are all visible on 3D-imaging.

As the present bowel filling negative contrast agent has no or only very mild side effects and high patients' acceptance, it is indicated as a preparatory agent in all patients referred for abdominal CT-examination, especially in those ill and sickly from the disease itself or its treatments.

A further embodiment, thus relates to the use of the present edible negative contrast agent, as contrast agent in CT imaging, such as CT imaging of the gastrointestinal tract including the intestines. Similarly, another embodiment relates to the present contrast agent for use as contrast agent in CT imaging, such as in CT imaging of the gastrointestinal tract including the intestines in a subject, e.g. a human being. Though the present edible negative contrast agent primarily is intended for use in human beings, it may be used in veterinary applications as well. Veterinary applications may for example include use in cats, dogs or horses, but is not limited thereto.

In CT imaging of the gastrointestinal tract including the intestines, the contrast agent may preferably be orally administered to the subject to be examined prior to the CT imaging. Especially, in CT imaging of the small intestine, an oral negative contrast agent is deemed to be an outstanding tool to overcome shortcomings in the art. The contrast agent may be for use in demarcation of at least the upper part of the small bowel in abdominal CT imaging. Preferably, the contrast agent may be for use in demarcation of the small bowel, from the duodenum and jejunum down to the colon.

Yet another embodiment relates to abdominal CT imaging method. The method comprises the step of:

orally administering the present edible negative contrast agent to the subject to be examined, e.g. a human being, to distribute it in the gastrointestinal tract including at least the upper part of the small intestine; and using a computerized tomography to obtain a CT-image of the subject's abdomen.

Further, the present edible negative contrast agent may not only be used in CT imaging of the gastrointestinal tract, but also in imaging of the gastrointestinal tract by abdominal MRI (magnetic resonance imaging) or abdominal ultrasound imaging, as dispersed air is useful as contrast agent also in such imaging techniques.

Thus, a further embodiment relates to the use of the present edible negative contrast agent, as contrast agent in imaging of the gastrointestinal tract by abdominal MRI or by abdominal ultrasound imaging. Similarly, another embodiment relates to the present contrast agent for use as contrast agent in imaging by abdominal MRI or abdominal ultrasound imaging, such as in MRI or ultrasound imaging of the gastrointestinal tract in a subject, e.g. a human being. Though the present edible negative contrast agent primarily is intended for use in human beings, it may be used in veterinary applications as well. Veterinary applications may for example include use in cats, dogs or horses, but is not limited thereto. Before abdominal MRI or abdominal ultrasound imaging, the contrast agent may preferably be orally administered to the subject to be examined prior to the imaging. Especially, in imaging of the small intestine, an oral negative contrast agent is deemed to be an outstanding tool to overcome shortcomings in the art. The contrast agent may be for use in demarcation of at least the upper part of the small bowel in abdominal MRI or ultrasound imaging.

Yet another embodiment relates to abdominal MRI and/or ultrasound imaging method. The method comprises the step of:
  orally administering the present edible negative contrast agent to the subject to be examined, e.g. a human being, to distribute it in the gastrointestinal tract including at least the upper part of the small intestine; and
  obtaining a MRI or ultrasound imaging image of the subject's abdomen.

As already described, the contrast agent may be provided by whipping an aqueous liquid composition comprising a surfactant, the surfactant being a protein, a hydrocolloid acting as foam stabilizer, a buffering agent; and water. The liquid composition may be provided by dispersing the other ingredients in water. Thus, a further embodiment relates to a dry composition for providing such a liquid composition. The dry composition comprises a surfactant, the surfactant being a protein, a hydrocolloid, and a buffering agent. Evidently, aspect already described in relation the surfactant, the hydrocolloid, and the buffering agent are equally applicable to the dry composition.

Thus, the dry composition according to an embodiment may comprise a natural gum, such as xanthan gum and/or propylene glycol alginate, as the hydrocolloid. Furthermore, the dry composition may comprise ovalbumin as the surfactant. According to an embodiment, the surfactant is egg albumen. In an embodiment wherein the surfactant is egg albumen the egg albumen may have been enzymatically treated with a protease. Treatment with a protease may improve the foamability and foam stability properties of egg albumen protein by reducing the molecular weight of the protein, increasing the number of ionizable groups, exposing hydrophobic aminoacids, and exposing functional groups that enhance intermolecular interactions.

According to another embodiment, in the dry composition:
  the weight ratio surfactant:hydrocolloid is from 10:1 to 1:1, such from 8:1 to 2:1;
  the content of the buffering agent is at least 20 wt %, such as at least 40 wt %;
  the content of the surfactant and the hydrocolloid all in all is at least 35 wt %, such as at least 50 wt %; and/or
  the content of the surfactant, the hydrocolloid, and the buffering agent all in all is at least 75 wt %, such as at least 85 wt %.

Further, the dry composition may according to such an embodiment optionally comprise at least 5 wt % of a flavoring agent.

According to another embodiment, in the dry composition:
  the weight ratio surfactant:hydrocolloid is from 10:1 to 1:1, such from 8:1 to 2:1;
  the content of the buffering agent is at least 30 wt %, such as at least 40 wt %;
  the content of the surfactant and the hydrocolloid all in all is at least 20 wt %, such as at least 35 wt %; and/or
  the content of the surfactant, the hydrocolloid, and the buffering agent all in all is at least 75 wt %, such as at least 85 wt %.

Further, the dry composition may according to such an embodiment optionally comprise at least 5 wt % of a flavoring agent.

According to another embodiment, in the dry composition:
  the weight ratio surfactant:hydrocolloid is from 10:1 to 1:1, such from 8:1 to 2:1;
  the content of the buffering agent is at least 10 wt %, such as at least 20 wt %;
  the content of the surfactant and the hydrocolloid all in all is at least 50 wt %, such as at least 60 wt %; and/or
  the content of the surfactant, the hydrocolloid, and the buffering agent all in all is at least 75 wt %, such as at least 85 wt %.

Further, the dry composition may according to such an embodiment optionally comprise at least 5 wt % of a flavoring agent.

As already described, such a dry composition may be prepared by freeze-drying or spray-drying an aqueous liquid composition comprising a surfactant, the surfactant being a protein, a hydrocolloid acting as foam stabilizer, a buffering agent, and water.

Without further elaboration, it is believed that one skilled in the art may, using the preceding description, utilize the present invention to its fullest extent. The preceding preferred specific embodiments are, therefore, to be construed as merely illustrative and not limitative of the disclosure in any way whatsoever.

Although the present invention has been described above with reference to specific embodiments, it is not intended to be limited to the specific form set forth herein. Rather, the invention is limited only by the accompanying claims and other embodiments than those specifically described above are equally possible within the scope of these appended claims, e.g. different embodiments than those described above.

In the claims, the term "comprises/comprising" does not exclude the presence of other elements or steps. Additionally, although individual features may be included in different claims, these may possibly advantageously be combined, and the inclusion of two features in different claims does not imply that a combination of those features is not feasible and/or advantageous.

In addition, singular references do not exclude a plurality. The terms "a", "an", "first", "second" etc. do not preclude a plurality.

Product Production

Materials

Food-Grade Substances

Mono- and di-potassium phosphate ($KH_2PO_4$, $K_2HPO_4$) and mono- and disodium phosphate ($NaH_2PO_4$, $Na_2HPO_4$) were supplied by Univar. High gel instant egg albumen powder (EAP-HGI or EWP-HGI), and regular, super high gel instant, and high whip instant egg albumen powders were supplied by Pulviver (Belgium). Keltrol®RD Xanthan gum was supplied by CP Kelco (Denmark). NPU protease was supplied by DSM Food Specialities BV. Flavours were provided by Symrise.

Substances Included in European Pharmacopeia

It should note that the substances mentioned above, apart from the egg albumen powders, as food-grade substances also are available in pharma-grade (cf. below).

Di-potassium phosphate and mono-sodium phosphate dihydrate were manufactured by Dr. Paul Lohmann, and supplied by Kemiintressen (Sweden). Xantural 11K were manufactured by CP Kelco (USA) and supplied by Kemiintressen (Sweden). Flavours were manufactured by Mane (France) and supplied by Kemiintressen (Sweden).

Devices, Instruments and Materials

Lab stirrer plate: RCT basic IKA Labortechnik (Non digital) and RCT basic IKA Safety control (Digital). Water baths: PRECISION water bath and GRANT water bath. Optical microscopy: Microscopy slide and cover slide silicone isolator (2 mm thick) and microscope connected with CellA, Imaging Software for Life Science Microscopy. Blender: Gastro 350 Bamix® equipped with a flat blade; Volumetric flask (500 mL and 1 L). 1 L thick glass wall beaker: 10 cm inner diameter, Schott Duran. 2 L thick glass wall beaker: 12.5 cm inner diameter, Schott Duran. 400 mL glass wall beaker: 7.5 cm inner diameter, Schott Duran. Magnetic stirring bars. PET jars RAMAPET R180 (1.5 L, 12.0 cm inner diameter) supplied by Neville and More (United Kingdom) and manufactured by Graham Packaging (Netherlands). PP caps used were from Neville and More, UK, (supplier), Macek, NL (manufacturer).

The Edible Negative Contrast Agent

Table 1 shows the composition of different formulations for the edible negative contrast agent used in the examples.

TABLE 1

Composition of different formulation of the edible negative contrast agent.

| No. | Buffer | EWP [%] | XG [%] | Flavour [%] | Air content [%] | Ingredients |
|---|---|---|---|---|---|---|
| 1 | Na$_2$HPO$_4$:KH$_2$PO$_4$ (75:25), 0.1M | 1[a] | 0.25 | 0.1-0.3 | 60 | Food-grade |
| 2 | K$_2$HPO$_4$:NaH$_2$PO$_4$ (75:25), 0.05M | 1[b] | 0.25 | 0.1-0.3 | 60 | Food-grade |
| 3 | K$_2$HPO$_4$:NaH$_2$PO$_4$ (75:25), 0.05M | 2[b] | 0.5 | 0.1-0.3 | 44 | Food-grade |
| 4 | K$_2$HPO$_4$:NaH$_2$PO$_4$ (75:25), 0.05M | 2[b] | 0.5 | 0.1-0.3 | 44 | Ph. Eu. |

[a]Enzymatic treatment with NPU protease.
[b]No enzymatic treatment.

All the material was carefully manipulated with gloves to avoid any possible contamination or traces of ethanol or fat that could interfere in the functionality properties of the egg white protein, and thus in the formability and foam stability.

The experimental procedure below shows the steps followed for the production of 500 mL of dispersion to obtain ca. 1.2 L of foam with 60% air content, since the volume required to be taken by adults to fill up the small bowel is between 0.9-1.2 L. In case that less air content is incorporated, larger volume of dispersion would be needed, i.e. 620 mL to obtain around 1.2 L of foam with 44% air content.

Ratios and amounts of ingredients in the product preparation below are specified in each example or formulation section and in Table 1.

Buffer Preparation

Phosphate buffer (500 mL) was prepared by dissolving the phosphate salts in dH$_2$O (500 mL) in a volumetric flask. The phosphate buffer was poured in a 1 L thick glass beaker, and both pH and temperature of the solution were determined.

Dispersion Preparation of High Gel Instant Egg White Protein (HGI-EWP)

HGI-EWP was dispersed in the filtered phosphate buffer (500 mL) at room temperature (22-23° C.) under stirring. The mixture was stirred until a completely homogenous dispersion was obtained. The dispersion was yellowish and turbid.

Enzymatic Treatment with NPU

NPU (0.005%) was added to the dispersion under stirring. The mixture was placed in a pre-stabilized water bath at 50° C. for 1 hour, moved to a pre-stabilized water bath at 70° C. for 15 minutes, and cooled down in an ice-water bath at 6° C. for 10 minutes.

Incorporation of Hydrocolloid (Xanthan Gum, XG)

Xanthan gum was added to the dispersion under continuous stirring until a homogenous dispersion was observed. The dispersion was yellowish and turbid.

Incorporation of Flavour

Flavour was added to the dispersion under stirring until complete homogenization.

At this point, the dispersion could be whipped to obtain a room temperature foam, or being stored in the fridge at 5±3° C. In case the dispersion was stored in a glass beaker covered with aluminum foil and sealed with parafilm, it could be stored for 1-2 days. In case the dispersion was stored in PET jar well closed with its lid, it could be stored for 1-2 days without preservative, or for at least 3 months under argon. Argon was used as preservative due to its antioxidant and anti-microbiological properties.

Foam Preparation

The homogenous dispersion (500 mL) containing all the components was transferred to a 2 L thick glass wall (12.5 cm inner diameter) or to a 1.5 L PET container (12.0 cm inner diameter) by pouring it towards the inner wall of container that was tilted to avoid the formation of big bubbles typically formed when the dispersion reaches the bottom directly from a certain height. It may be preferred to avoid spreading dispersion above the final foam volume when transferring dispersion to ensure that the entire dispersion was incorporated and converted into foam, even though it was observed that the foam properties were not affected by remaining dispersion that was spread and stuck on the container wall above the final foam volume.

An overrun within 70-140%, corresponding to approximately 40-60% air content, provides a foam with well accepted consistency (between 7.5-12 cm) by patients and an optimal negative density contrast values (between minus 400 and minus 650 HU) in x-ray imaging. According to an embodiment, the overrun is around 140%, corresponding to approximately 60% air content. Such a foam has a well-accepted consistency (typically 8.5-12 cm) by patients and provides good negative density contrast values. An optimal air content is crucial to find a good balance between optimal consistency and optimal negative density contrast. The air content should be high enough to give a good negative density contrast but at the same time the air content cannot be too high to obtain foams that flow well and easily (too stiff foams would make the foam to be hard to drink or even spoonable).

The dispersion was whipped using a flat blade in 2 L glass beaker or in 1.5 L PET container in a process divided into two main steps:

1) Incorporation of Air and Foam Formation.

The dispersion started to be whipped using a flat blade and the blender was slowly moved vertically upwards while bubbles were formed and until the desired final volume was reached. At this point the blender was moved stopped and moved vertically downwards. The process of starting the foam formation was carefully performed to avoid the formation of too many and too big bubbles that would be notably hard to break up to obtain a homogenous foam.

2) Break Up Big Bubbles to Obtain a Homogeneous Foam with Small Bubble Size and Low Polydispersity.

The blender was moved in vertical movements in complete displacement upwards and downwards from the upper and lower limits, being the upper limit the final desired foam volume and the lower limit the bottom of the container (without crashing it). The blade of the blender was continuously kept in the dispersion without creating any air pocket to avoid the incorporation of extra air and the formation of new big bubbles. Every time the blender was taken upwards, it was preferred to keep the blender at the upper limit for few extra seconds to break up more efficiently the big bubbles remaining at the surface. Significant attention was paid when bringing the blade very close to the surface to avoid the incorporation of excess air because it would cause an increase in overrun and consequently thicker foam, as well as the formation of new big bubbles giving a non-homogenous and high polydispersity foam. Such a foam would negatively interfere with the quality of the x-ray images.

The foam should not comprise any clearly visible bubbles among the microbubbles that the foam is made up of. Thus, the foam was whipped until the foam was homogenous and with no visible bubbles. In case a small amount, such 1-15 units, of isolated visible bubbles were detected by bear eye at the surface of the foam, the bubbles were removed with a spoon or with a suction device such as a Pasteur pipette. If too many bubbles that may not be removed were present at the surface and/or in the bulk, the foam may be have to be discarded. Alternatively, the foam may be re-whipped.

The whipping process to obtain around 1.2 L of homogenous foam with 40-60% air content may take around 5±1 min.

Foam Characterization

Five parameters were determined to characterize the edible negative contrast agent: amount of air, bubble size, pH, stability and consistency.

The amount of air incorporated in the foam can be given in terms of overrun (%), which was determined by weight, or in terms of air content (%), which was determined by volume. The overrun is defined as the percentage of gas-to-liquid ration in aerated systems and it was determined by weight by using the equation below [Eq. 1], $$\text{Overrun} = [(W_d - W_f)/W_f] \times 100 \quad [\text{Eq. 1}]$$

where $W_d$ is the weight of a given volume of the dispersion, and $W_f$ is the weight of foam for the same volume than the dispersion. The dispersion and the foam were weighed in a 4 cL plastic cup by filling it up and leveling with a spatula with neither bubbles nor air pockets in neither the bulk nor the surface. The air content was determined by percentage of air volume in the total volume of foam [Eq. 2].

$$\text{Air content} = (V_{air}/V_{foam}) \times 100 \quad [\text{Eq. 2}]$$

The bubble size (diameter, d) was measured by transferring 0.5 mL of foam (with a 3 mL Pasteur pipette) to a cover slide with a silicon isolator (2 mm thick) and covered with a glass slide. The bubble size was determined by optical imaging using an optical microscope connected with CellA, Imaging Software and applying $4^\times$ magnification. After screening the sample and checking that the bubble size distribution was homogeneous, the mean value of the bubble size was considered to be the third largest bubble The pH and temperature of the foam was determined by using a pH-meter equipped with temperature sensor.

Stability with time and temperature. The stability was assessed by determining the three parameters above at different times (time 0—right after the foam formation—, and every 5, 10 and/or 20 minutes up to at least 2 hours) and at room temperature (22-23° C.). In addition to the assessment of the evolution of overrun, bubble size and variation in pH, it was also assessed the life-time of the foam in glass beaker, PET container and/or in cylinders by measuring liquid drainage observed with time by bare eye. In order to clearly detect liquid drainage and avoid neglecting any, the foam was exposed to white natural light lamp and the beaker or container was tilted in order to facilitate the liquid detection by bringing to the edge any tiny liquid volume that could be spread and not visible at the bottom.

Consistency (distance of flow). The distance of flow of the foams was measured using a standard 30 cm scaled Bostwick consistometer (CSC Scientific Co. 24925-000. UNSPSC code 41112501. EAN 0795871687145, 0791836540258. UPC 795871687145, 791836540258) in accordance with ASTM F1080-93(2013) apart from omitting step 5.2 (agitation) thereof. In short, the sample compartment (width b=5 cm; height H=4 cm; b/H=1.3; $V=b^2H=100$ cm$^3$) was entirely loaded and leveled with foam (approximately 100 mL). To facilitate the fluid flow, the consistometer sits at a certain angle which is usually neglected. The gate was sharply opened, and the distances traveled through a stainless steel track (24 cm length with 0.5 cm graduation, and 5 cm wide) by the leading and the sides edges of the foam after 30 sec. were recorded and averaged over 3-4 consecutive measurements.

Feasibility in the Gastrointestinal Tract, In Vitro Studies

In vitro digestive tests were performed on 500 mL of foam. The results were always compared with the evolution of a foam control that was exposed to physical stress (temperature and mimicked peristaltic movements) but not chemical stress (gastrointestinal juices).

Material

Pepsin from porcine gastric mucosa (P6887, 3200-4500 U/mg) and Pancreatin from porcine pancreas (P7545, 8×USP) were supplied by Sigma-Aldrich. Ursolfalk was provided by Dr. Falk Pharma GmbH (Germany).

Method

Pepsin (2.64 mg, 37 U/ml) was dissolved in HCl (0.01 M, 0.5 mL) at ca. 30° C., and dropwise and slowly added to the foam (500 mL) previously stabilized in a water bath at 37° C. The foam with the added gastric juice was very gently homogenized by using a plastic flat wide spatula (manual stirring for 40 seconds) and incubated under orbital shaking at 80 mot/min for 30 minutes or 1 hour at 37° C. together with the foam control. Then, pancreatin (25 mg, 10 U/mL) in NaHCO$_3$ (0.1 M, 7 mL) mixed with Ursofalk (2 mL) was dropwise and slowly added to the foam, which was homogenized by manual stirring with a wide flat plastic spatula for 40 seconds. The foam was incubated under orbital shaking at 80 mot/min for 30 minutes or 1 hour at 37° C. together with the foam control.

The final foams were characterized by determining overrun, bubble size, pH, stability, and also by CT-imaging.

The 2-hours total incubation time for both gastric and intestinal treatment was significantly longer than the time that the foam would normally stay in the stomach and proximal small bowel of patient with no acute abdominal symptoms. The incubation time was chosen to ensure that the foam was exposed long enough to mimic the anticipated in vivo time for foam in the entire small bowel. 1 hour at each stage is usually in case of digestion of solid food, but the time is notably decreased to around 15-30 minutes at each stage in case liquids. The given mean time for solid food to be processed in the stomach and passage time as a bolus through the whole small bowel is approximately one hour each. These times are notably shorter for liquids.

Foam Stability and Negative Contrast Assessment by CT Imaging

CT imaging assessment was performed at the Radiology department at the University Hospital in Malmö (Bild-och Funktionsmedicin, SUS, Malmö) by using a Siemens Somatom 16 (Siemens AG, Forcheim, Germany) CT. Radiation dose was applied with a tube kilovoltage of 120 kV and a reference mAs of 100. Images were presented in 0.75 mm thick slices and reconstructed in coronal and sagittal views Batches of foams were tested in vitro simultaneously, one that had not been exposed to gastric- and duodenal stress treatment served as a control. The foams were gently poured in U-shape, hard plastic tubes, which were submerged in 30 cm of tap water at body heat (ca. 37° C.) in order to mimic the density of the body.

The container with foam filled tubes was placed in a CT-machine for cross sectional examination using the same exposure data as for a clinical abdominal CT-examination. The study images were presented in axial, coronal and sagittal projections. The CT-scan images allowed the evaluation of:

Foam instability disclosed as a foam-liquid level (i.e. phase separation) at the bottom of the tubes.

Foam homogeneity seen as absence of bigger bubble size formation, usually in clusters.

Foam contrast by measuring the density in HU units in mid lumen of the foam filled tubes.

Feasibility in the Gastrointestinal Tract, In Vivo Study. Clinical Trials in Healthy Volunteers Method Healthy volunteers gave their written consent to participate in this feasibility study. They were offered to drink four cups of freshly prepared foam for a clinical test of the negative contrast agent Immediately after drinking all underwent imaging with computerized tomography of the abdomen. A clinical abdominal protocol without intravenous iodine contrast was chosen with the individual in supine position in a Siemens Somatom 16 (Siemens AG, Forcheim, Germany). The CT examination was performed using the lowest possible radiation dose for adults with a tube kilovoltage of 120 kV and a reference mAs of 40. Images were presented in 1 mm thick slices and reconstructed in coronal and sagittal views.

Although all foam ingredients were food based and within safety limits, blood samples were taken to control serum electrolyte levels of sodium, potassium and phosphorous in order to disclose any hyperphosphatemia and electrolyte imbalance from sodium and potassium containing buffer solutions. Moreover, calcium was also controlled since hyperphosphatemia can cause hypocalcemia. Blood samples were taken 5-15 minutes before foam intake and around 1 hour 30 minutes after the first sip and/or 5-45 minutes after the last sip of the negative contrast agent.

Three hours after a light breakfast, volunteers uninterruptedly drank 0.9-1.5 L of foam divided into doses (0.30-0.37 L each) in approximately 1 hour (12-15 min per dose), either by drinking directly from the cup, or using a 1 cm diameter straw, or a tablespoon. The subjects were encouraged to walk for at least 5-15 minutes during the intake, not only to promote intestinal transit but also to diminish feeling of fullness thereby promoting the ability to take the entire volume. In case of fullness, volunteers were permitted to abstain from the intake of the last dose.

Evaluation and Feasibility Assessment of the Foam as Bowel Filling Agent with Negative Contrast Agent Properties on Radiological Images from Abdominal CT-Scan Examination Negative density contrast values were determined at 3 different points to average each of six parts of the gastrointestinal tract (stomach, duodenum, jejunum, proximal ileum, distal ileum, terminal ileum) and cecal part of colon. The image quality and foam filling of the loops of small bowel were also assessed in a 4-points scale. Likewise, palatability, drinkability, degree of fullness, ease of intake and side effects and other comments were evaluated by interviewing the subjects before and during the intake, as well as immediately after the CT-examination and 24 hours later. Venous blood was sampled in each for routine analyses of serum electrolytes before the foam intake and after the CT-examination.

Example 1

Formulation 1

Foams were prepared with food-grade ingredients, phosphate buffer $Na_2HPO_4:KH_2PO_4$ ((75:25), 0.1 M, pH 7.3), EWP (1 wt %), XG (0.25%), flavor (0.1-0.3 wt %).

The edible negative contrast agent showed the following characterization:

Overrun: around 140% (60% air content)

Bubble size (diameter): d=70-80 μm pH 7.3 (22° C.)

Consistency: 9.8 cm

Dry matter: 2.5%

Palatability: Acceptable to drink but salty flavor.

Stability: Foams in a glass beaker covered with aluminum foil, showed life-time (no liquid drainage at all) for around 1 h 5 min which is longer time than the time required for both the foam intake and the CT-abd examination.

Feasibility in In Vitro Digestive Test

The characterization of the foam was performed at the end of the entire digestive treatment to avoid any interruption between the gastric and the intestinal digestion in terms of temperature, mechanical stress, and any further evolution of the digestive enzyme. The foam showed an increase in overrun of around 20%. The pH remained stable (pH 7.3). Liquid drainage was observed, most of it likely corresponded to the 9.5 mL of gastrointestinal juices added during the test, so only 1.3% of the total foam volume was liquid that drained from the continuous aqueous phase of the foam, which may be mixed and homogenized by the peristaltic movements of the gut. It is worth to mention that the in vitro test was performed for a total of 2 hours instead of the expected 1 hour. Moreover, the volume of gastrointestinal fluid is expected to be notably lower than the added for two reasons: a) the subject will be in fasted state, b) it is to be presumed that the composition of high air and low amount of egg protein will induce only a minimal mucosal stimulation to produce gastro-intestinal juices.

CT Imaging

Transversal, coronal and cross-sectional x-ray images were obtained in abdominal window—which is the window used for diagnosis and HU measurements—.

The foams were homogenously distributed along the tubes, no interferences from big bubbles were detected, and the measured negative density contrast values were between minus 530 and minus 725 HU. The liquid drainage mentioned above was observed at the bottom on of the tubes.

Feasibility in In Vivo Test (Clinical Trial)

Twenty-five healthy volunteers between 50 and 75 years old (Table 2a) participated in the study. 40% were between 50-59 years old, 52% between 60-69, and 8% between 70-75 years of age (Table 2b). In terms of gender, 48% male and 52% female. The mean age was 61 years old.

TABLE 2a

Number of healthy volunteers of a certain gender and age range that participated in the Clinical study.

| | Age (years old) | | | | |
|---|---|---|---|---|---|
| | 40-49 | 50-59 | 60-69 | 70-75 | Total |
| Male | 0 | 5 | 6 | 1 | 12 |
| Female | 0 | 5 | 7 | 1 | 13 |
| Total | 0 | 10 | 13 | 2 | 25 |

TABLE 2b

Gender and age of healthy volunteers that participated in the Clinical study.

| No. | Gender | Birth year | Age | Male average | Female average | Total average |
|---|---|---|---|---|---|---|
| 01 | Male | 1960 | 56 | 62 | 61 | 61 |
| 02 | Male | 1959 | 57 | | | |
| 03 | Male | 1945 | 71 | | | |
| 04 | Male | 1950 | 66 | | | |
| 05 | Male | 1958 | 58 | | | |
| 06 | Female | 1953 | 63 | | | |
| 07 | Male | 1948 | 68 | | | |
| 08 | Male | 1964 | 52 | | | |
| 09 | Female | 1956 | 60 | | | |
| 10 | Female | 1945 | 71 | | | |
| 11 | Female | 1956 | 60 | | | |
| 12 | Female | 1964 | 52 | | | |
| 13 | Male | 1951 | 65 | | | |
| 14 | Female | 1963 | 53 | 62 | 59 | 60 |
| 15 | Male | 1951 | 65 | | | |
| 16 | Female | 1963 | 53 | | | |
| 17 | Female | 1951 | 65 | | | |
| 18 | Male | 1950 | 66 | | | |
| 19 | Female | 1956 | 60 | | | |
| 20 | Female | 1956 | 60 | | | |
| 21 | Male | 1958 | 58 | | | |
| 22 | Female | 1958 | 58 | | | |
| 23 | Female | 1962 | 54 | | | |
| 24 | Female | 1951 | 65 | | | |
| 25 | Male | 1956 | 60 | | | |
| Total | | | | 62 | 60 | 61 |

CT-scan results mostly showed consistent negative contrast values all along the gastrointestinal tract, between minus 400 and minus 700 HU, except for short sections that were not or insufficiently filled with the negative contrast agent (Table 3a). No foam degradation of the negative contrast agent was evident from the CT-examinations. Region of interest (ROI)-values (ROI-diameter 6-8 mm) were calculated for each of seven sub-segments of the small bowel. The mean intraluminal HU-value of the foam ranged from minus 400 HU to minus 700 HU. The extreme values may be explained by peristalsis, by incorporation of pre-existing bowel solids and by pushing endogenous gas ahead towards lower segments, i.e. amplified HU-negativity. The measured mean values indicate agent stability during time of examination. In an attempt to improve filling of the first part of the small bowel, i.e. the duodenum and jejunum, the last 10 volunteers were asked to rest for a few minutes on their right side. FIG. 2 shows an example of CT-images. From CT-scan images of distal and axial sections at different sections of the gastrointestinal tract, quality of CT-images, and foam filling and distribution were evaluated (Table 3b.1-3). Moreover, the observations below were also noted:

- The optimal drinking time to fill up the entire length of the gut with foam was observed to be one hour. A too fast or too anxious and/or overwhelmed drinking may result in a discontinuous and spotted distribution. The reason for a smooth, constant, and homogeneous transit of the negative contrast agent to be disrupted may be attributed to individual variations in the gut physiology and personality.
- To drink continuously and evenly (12-15 min per dose) and directly from the cup was shown to result in good bowel filling and continuous distribution. The use of straw or tablespoon might promote gulping down undesired air easily detected on CT-scan images as endogenous air. Furthermore, swallowed air may give rise to an uneven foam distribution, spotted and discontinuous, as well as an air lock in the small bowel.
- 1 L of negative contrast was observed to be optimal to fill up the gastrointestinal tract in the majority of volunteers. In a minority of subjects, it will not be possible to get a perfect filling of the most distal part of the small bowel. This problem is well known to every gastro-intestinal radiologist and modern techniques have not been helpful to overcome the problem. The success in complete filling of the gut is considered to be uncertain due to the significant variations in physiology of the digestive system and psychology from one person to another (amount of endogenous air/liquid, gut motility, digestive transit, degree of relaxation of the small bowel, etc). In fact, not all volunteers that took 1.4 L showed a complete filling, while other volunteers showed properly filled bowel loops with only 0.9 L.
- A gentle physical exercise, viz. walking around for 15 to 20 minutes during the intake resulted in an overall improved filling and distribution of the foam.
- Lay down on the right side for 15-20 minutes after drinking up the required volume of foam boosted the filling of the duodenum and jejunum before the CT-abd examination.
- A minimum of 3 hours fasting after a light breakfast is required.
- No serious side effects were reported. Volunteers experienced bloating, occasional flatulence or burping, that were not especially uncomfortable and that were dissipated in 1-2 hours (or around 8 hours in 2-3 cases) after walking, drinking or eating.
- The serum phosphate levels increased in all subjects. The mean increase was 0.56 mmol/L (53%) and for no subject the increase exceeded 160%, the upper range of normality. In two female subjects, serum phosphate increased from 1.5 mmol/L before to 2.2 and 2.4 mmol/L after drinking, exceeding the normal upper limit with 0.7 mmol/L and 0.9 mmol/L respectively. No changes were seen in serum levels of sodium, calcium or potassium, which all remained within the normal ranges.

The taste and foamy consistency was deemed acceptable by all subjects. Six volunteers remarked difficulty with the last (fourth) cup, two of whom refrained from drinking after having had 0.9 L.

Observed side effects were all mild with no need to intervene. Eructation was reported by seven volunteers, abdominal distension by four, nausea by three, abdominal discomfort by one, and flatulence by two during and two others after drinking. Two volunteers mentioned single episodes of loose stools in the morning. All related side effects are presented in Table 3b.4. For all subjects, the following night sleep was undisturbed with no prevailing side effect. Daily eating habits were not influenced.

TABLE 3a.1

Negative density contrast values determined along the initial sections of the gastrointestinal tract of healthy volunteers in CT-scan tests.

| Subject No. | Contrast density value [HU] | | |
|---|---|---|---|
| | Stomach | Duodenum | Jejunum |
| 01 | −580 ± 18 | −538 ± 36 | −564 ± 52 |
| 02 | −591 ± 15 | −497 ± 97 | — |
| 03 | −599 ± 26 | — | −587 ± 40 / −589 ± 21 |
| 04 | −589 ± 24 | −626 ± 45 | −566 ± 23 |
| 05 | −550 ± 28 | −641 ± 26 | −542 ± 43 / −582 ± 20 |
| 06 | −603 ± 30 | −580 ± 55 | −580 ± 20 |
| 07 | −600 ± 35 | −650 ± 50 | −530 ± 50 |
| 08 | −600 ± 30 | — | −420 ± 15 |
| 09 | −560 ± 25 | −517 ± 18 | — |
| 10 | −630 ± 20 | −650 ± 30 | −450 ± 60 |
| 11 | −580 ± 15 | −490 ± 35 | −530 ± 50 |
| 12 | −600 ± 35 | −640 ± 00 | −560 ± 25 |
| 13 | −600 ± 40 | — | −560 ± 40 |
| 14 | −560 ± 16 | −510 ± 45 | −625 ± 30 |
| 15 | −650 ± 15 | −620 ± 80 | −560 ± 80 |
| 16 | −600 ± 20 | −575 ± 15 | −550 ± 10 |
| 17 | −600 ± 35 | — | −575 ± 25 |
| 18 | −580 ± 20 | −570 ± 12 | −570 ± 15 |
| 19 | −600 ± 5 | — | −650 ± 10 |
| 20 | −600 ± 20 | −550 ± 20 | −600 ± 35 |
| 21 | −550 ± 20 | −570 ± 30 | −500 ± 40 |
| 22 | −575 ± 20 | — | −575 ± 25 |
| 23 | −580 ± 40 | — | −420 ± 50 |
| 24 | −560 ± 30 | −540 ± 60 | −570 ± 60 |
| 25 | −560 ± 40 | — | −570 ± 15 |

TABLE 3a.2

Negative density contrast values determined along the ileum of healthy volunteers in CT-scan tests.

| Subject No. | Contrast density value [HU] | | | |
|---|---|---|---|---|
| | Proximal ileum | Middle ileum | Distal ileum | Terminal ileum |
| 01 | −477 ± 16 | −497 ± 11 | −663 ± 81 | — |
| 02 | −579 ± 35 | −550 ± 92 | +37 ± 17 | +41 ± 28 |
| 03 | | −682 ± 22 / −691 ± 77 | From −426 ± 49 to −744 ± 44 / −554 ± 38 | −573 ± 28 / −963 ± 41 (endogenous air) |

TABLE 3a.2-continued

Negative density contrast values determined along the ileum of healthy volunteers in CT-scan tests.

| Subject No. | Contrast density value [HU] | | | |
|---|---|---|---|---|
| | Proximal ileum | Middle ileum | Distal ileum | Terminal ileum |
| 04 | — | −566 ± 23 | −516 ± 40 | +28 ± 14 |
| 05 | From −434 ± 115 to −505 ± 78 [a] | From −520 ± 52 to −539 ± 89 [a] | From −552 ± 79 to −611 ± 29 [a] | |
| 06 | −620 ± 38 | −600 ± 70 | −600 ± 50 | −650 ± 15 |
| 07 | −600 ± 40 | −630 ± 50 | −630 ± 0 | −600 ± 50 |
| 08 | −525 ± 35 | −580 ± 65 | −500 ± 40 | −450 ± 22 |
| 09 | — | −670 ± 50 | −425 ± 90 | −990 ± 27 |
| 10 | −680 ± 40 | −570 ± 40 | −700 ± 40 | — |
| 11 | −630 ± 40 | −630 ± 50 | −710 ± 15 | −580 ± 30 |
| 12 | −620 ± 50 | −630 ± 40 | −620 ± 35 | −600 ± 40 |
| 13 | −590 ± 70 | −700 ± 40 | −600 ± 70 | −575 ± 20 |
| 14 | −500 ± 15 | −500 ± 60 | −600 ± 35 | −670 ± 15 |
| 15 | −590 ± 20 | −400 ± 60 | −650 ± 20 | −580 ± 60 |
| 16 | −630 ± 20 | −630 ± 15 | −580 ± 20 | −700 ± 5 |
| 17 | −680 ± 30 | −650 ± 30 | −570 ± 30 | — |
| 18 | −500 ± 20 | −600 ± 0 | −610 ± 30 | −480 ± 25 |
| 19 | −640 ± 0 | −612 ± 0 | −450 ± 70 | −700 ± 20 |
| 20 | −550 ± 30 | −600 ± 45 | −600 ± 30 | −650 ± 15 |
| 21 | −560 ± 20 | −630 ± 15 | −525 ± 30 | −400 ± 25 |
| 22 | −580 ± 25 | −610 ± 75 | −990 ± 10 | — |
| 23 | −590 ± 40 | −500 ± 50 | −590 ± 40 | −980 ± 20 |
| 24 | −530 ± 60 | −520 ± 60 | −500 ± 125 | −530 ± 50 |
| 25 | −500 ± 25 | −570 ± 30 | −610 ± 25 | −570 ± 20 |

[a] Mean value between those mean values. There is a partial volume effect due to the lack of bowel distention.

TABLE 3a.3

Additional information during CT-scan examination.

| Subject No. | Time between last sip and CT-scan [min] | Intake time [min] | Way of intake |
|---|---|---|---|
| 01 | 28 | 37 | Straw and spoon (2:2) |
| 02 | 7 | 20 | Drank |
| 03 | 23 | 58 | Straw and spoon (1:3) |
| 04 | 9 | 60 | Straw |
| 05 | 10 | 61 | Drank |
| 06 | 20 | 56 | Spoon |
| 07 | 12 | 59 | Spoon |
| 08 | 6 | 55 | Drank |
| 09 | 30 | 48 | Drank |
| 10 | 10 | 54 | Drank |
| 11 | 4 | 48 | Drank |
| 12 | 2 | 53 | Drank |
| 13 | 3 | 58 | Mostly straw |
| 14 | 1 | 56 | Drank |
| 15 | 2 | 49 | Drank |
| 16 | 5 | 59 | Drank (mostly sitting) |
| 17 | 8 | 41 | Drank (mostly sitting) |
| 18 | 19 | 61 | Drank (walked 4 min) |
| 19 | 12 | 59 | Drank (mostly sitting) |
| 20 | 19 | 72 | Drank (moving around whole time) |
| 21 | 22 | 43 | Drank (walked 3-5 min) |
| 22 | 20 | 37 | Drank (walked 15 min) |
| 23 | 10 | 42 | Drank (walked 15 min) |
| 24 | 14 | 39 | Drank (walked 15 min) |
| 25 | 29 | 49 | Drank (walked 24 min) |

TABLE 3a.4

Mean intra luminal ROI-values in seven parts of the gastrointestinal tract after treatment. Figures denote Hounsfield units. The ROI was typically set to 6 mm in diameter. Range denote the highest and lowest HU recorded per segment.

| Part of bowel | HU mean | HU, range | Number of patients |
|---|---|---|---|
| Stomach | −566 | −560 to −600 | n = 25 |
| Duodenum | −530 | −490 to −650 | n = 17 |
| Jejunum | −560 | −490 to −650 | n = 24 |
| Proximal ileum | −530 | −477 to −530 | n = 24 |
| Middle ileum | −570 | −491 to −700 | n = 25 |
| Distal ileum | −570 | −425 to −700 | n = 25 |
| Terminal ileum | −540 | −470 to −650 | n = 20 |

TABLE 3b.1

Assessment of image quality and foam appearance in CT-scan images of the initial sections of the gastrointestinal tract.

| Subject No. | Gender | Stomach Q | Stomach F | Duodenum Q | Duodenum F | Jejunum Q | Jejunum F |
|---|---|---|---|---|---|---|---|
| 01 | m | 1 | 1 | 2 | 2 | 2 | 1 |
| 02 | m | 1, 3 | 1 | 2 | 2 | 1 | 1 |
| 03 | m | 1, 3 | 1 | 3 | 3 | 1 | 2 |
| 04 | m | 1, 3 | 2 | 1 | 1 | 1 | 1 |
| 05 | m | 1, 3 | 1 | 2 | 1 | 1 | 1 |
| 06 | f | 1, 3 | 2 | 2 | 2 | 1 | 1 |
| 07 | m | 1, 3 | 1 | 2, 4 | 3 | 1 | 2 |
| 08 | m | 1, 3 | 1 | 0 | 0 | 1, 4 | 2 |
| 09 | f | 1, 3 | 1 | 1 | 2 | 0 | 0 |
| 10 | f | 1 | 1 | 1 | 1 | 1 | 1 |
| 11 | f | 1, 3 | 1 | 1 | 2 | 1 | 2 |
| 12 | f | 1, 3 | 1 | 1 | 1 | 1 | 2 |
| 13 | m | 1, 3 | 2 | — | 0 | 1 | 2 |
| 14 | f | 1, 3 | 2 | 2 | 2 | 1 | 1 |
| 15 | m | 1, 3 | 1 | 2 | 3 | 2 | 3 |
| 16 | f | 1, 3 | 1 | 2 | 2 | 2 | 2 |
| 17 | f | 1, 3 | 1 | — | 3 | 1 | 2 |
| 18 | m | 1, 3 | 1 | 2 | 3 | 1 | 1 |
| 19 | f | 1, 3 | 2, 3 | — | 3 | 1 | 2 |
| 20 | f | 1, 3 | 2 | 2 | 2 | 2 | 1 |
| 21 | m | 1, 3 | 1 | 2 | 2 | — | 1 |
| 22 | f | 1, 3 | 2 | 3 | 0 | 2 | 1, 4 |
| 23 | f | 2, 3 | 2 | 4 | 2, 3 | 2 | 2 |
| 24 | f | 1, 3 | 1 | 2 | 1 | 2 | 2, 4 |
| 25 | m | 2, 3 | 2 | — | 0 | 1 | 2 |

[a]Quality of CT-scan image. Homogeneous: 1, Separation: 2, Endogenous gas: 3, Endogenous liquid: 4.
[b]Filling. None: 0, Good: 1, Quite good: 2, Bad: 3.

TABLE 3b.2

Assessment of image quality and foam appearance in CT-scan images of the final sections of the gastrointestinal tract.

| Subject No. | Gender | Proximal ileum Q | Proximal ileum F | Middle ileum Q | Middle ileum F | Distal ileum Q | Distal ileum F | Terminal ileum Q | Terminal ileum F | Colon F |
|---|---|---|---|---|---|---|---|---|---|---|
| 01 | m | 1 | 1 | 1 | 1 | 2 | 0 | 0 | 0 | 0 |
| 02 | m | 1 | 1 | 2 | 1 | 0 | 3 | 0 | 0 | 0 |
| 03 | m | 2 | 1 | 2 | 1 | 1 | 1 | 1 | 1 | 0 |
| 04 | m | 2 | 1 | 1 | 2 | 2 | 2 | 0 | 0 | 0 |
| 05 | m | 1 | 1 | 1 | 1 | 1 | 2 | 2 | 2 | 1 |
| 06 | f | 1 | 1 | 1 | 1 | 1 | 1 | 2 | 2 | 1 |
| 07 | m | 1 | 2 | 2 | 2 | 2 | 3 | 1 | 1 | 1 |
| 08 | m | 1 | 1 | 1 | 1 | 2 | 2 | 2 | 1 | 1 |
| 09 | f | 0 | 0 | 2 | 2 | 2 | 2 | 1 | 1 | 0 |
| 10 | f | 1 | 1 | 1 | 1 | 1 | 1 | — | 3 | 0 |
| 11 | f | 2 | 1 | 2 | 1 | 2 | 1 | 1 | 2 | 0 |
| 12 | f | 1 | 1 | 1 | 1 | 1 | 1 | 1 | 2 | 1 |
| 13 | m | 2 | 1 | 2 | 1 | 2 | 1 | 2 | 2 | 1 |
| 14 | f | 1 | 1 | 1 | 1 | 1 | 1 | 2 | 2 | 1 |
| 15 | m | 1 | 1 | 1 | 1 | 1 | 1 | 2 | 2 | 1 |
| 16 | f | 1 | 1 | 1 | 1 | 1 | 1 | 2 | 2 | 1 |
| 17 | f | 1 | 1 | 1 | 1 | 1 | 1 | — | — | — |
| 18 | m | 2 | 2 | 2 | 2 | 2 | 2 | 2 | 2 | 3 |
| 19 | f | 1 | 1 | 1 | 1 | 1 | 1 | 2 | 2 | 0 |
| 20 | f | 2 | 2 | 1 | 1 | 1 | 1 | 1 | 1 | 2 |
| 21 | m | 1 | 1, 3 | 2 | 3 | 1 | 1 | 2 | 1 | 3 |
| 22 | f | 1 | 1 | 1 | 1 | 2 | 3 | 0 | 0 | 0 |
| 23 | f | 1 | 1 | 1 | 1 | 1 | 1 | 1 | 0 | 3 |
| 24 | f | 2 | 2 | 2 | 1 | 2 | 2 | 1 | 1 | 2 |
| 25 | m | 1 | 1 | 1 | 1 | 2 | 2 | 1 | 2 | 1 |

[a]Quality of CT-scan image. Homogeneous: 1, Separation: 2, Endogenous gas: 3, Endogenous liquid: 4.
[b]Filling. None: 0, Good: 1, Quite good: 2, Bad: 3.

TABLE 3b.3

Assessment of image quality and foam appearance in CT-scan images.

| Subject No. | Gender | Distribution[a] | Enterography[b] | Volume taken (ca.) [L] |
|---|---|---|---|---|
| 01 | Male | 3 | 2 | 1.2 |
| 02 | Male | 3 | 2 | 1.2 |
| 03 | Male | 2 | 1 | 1.3 |
| 04 | Male | 2 | 2 | 1.3 |
| 05 | Male | 2 | 2 | 1.4 |
| 06 | Female | 1 | 3 | 1.4 |
| 07 | Male | 3 | 2 | 1.4 |
| 08 | Male | 2 | 2 | 1.4 |
| 09 | Female | 3 | 2 | 0.9 |
| 10 | Female | 2 | 3 | 1.4 |
| 11 | Female | 2 | 2 | 1.4 |
| 12 | Female | 2 | 2 | 1.4 |
| 13 | Male | 2 | 2 | 1.4 |
| 14 | Female | 2 | 3 | 1 |
| 15 | Male | 2 | 2 | 1.4 |
| 16 | Female | 1, 2 | 2 | 1.4 |
| 17 | Female | 2 | 2 | 1.4 |
| 18 | Male | 3 | 2 | 1.4 |
| 19 | Female | 2 | 2 | 1.4 |
| 20 | Female | 3 | 2 | 1.4 |
| 21 | Male | 2 | 2 | 1.4 |
| 22 | Female | 3 | 2 | 1.2 |
| 23 | Female | 2 | 2 | 1 |
| 24 | Female | 3 | 3 | 1.2 |
| 25 | Male | 2 | 2 | 1.3 |

[a]Distribution: Continuous: 1, Good: 2, Discontinuous/patchy: 3
[b]Enterography: Yes: 1, No: 2, Doubtful: 3

TABLE 3b.4

Number of treated subjects with related (investigators assessment) AEs by preferred term (MedDRA) and severity after treatment (N = 25).

| System Organ Class | Preferred Term | Mild n (%) | Moderate n (%) | Severe n (%) | Total n (%) |
|---|---|---|---|---|---|
| Gastrointestinal Disorders | Abdominal discomfort | 1 (4%) | — | — | 1 (4%) |
| | Abdominal distension | 4 (16%) | — | — | 4 (16%) |
| | Diarrhoea [1] | 2 (8%) | — | — | 2 (8%) |
| | Eructation | 7 (28%) | — | — | 7 (28%) |
| | Flatulence | 2 (8%) | — | — | 2 (8%) |
| | Nausea | 3 (12%) | — | — | 3 (13%) |

[1] Reported terms were single episodes of loose morning motion

Example 2

Assessment of Buffer

Monophosphate:Diphosphate Ratio

Disodium phosphate:monopotassium phosphate ($Na_2HPO_4$:$KH_2PO_4$) (50:50) provides with buffer pH 6.8 with good buffer capacity at both acid and alkaline environments, while disodium phosphate:monopotassium phosphate ($Na_2HPO_4$:$KH_2PO_4$) (75:25) provides with buffer pH 7.3 with significantly better buffer capacity in acid environments than alkaline. The second ratio was chosen for the following reasons:

a) Egg white protein functionality are enhanced by increasing its dispersability which was observed to improve at pH 7.3.

b) The small bowel and intestinal juices pH are slightly below the neutral pH, while the stomach pH is significantly acid (pH 1-3). Thus, the buffer capacity may be stronger to face acid rather than alkaline environment.

For these two reasons 75:25 ratio of monophosphate:diphosphate was chosen as the optimal buffer. Experimental results confirmed the optimal protein dispersion preparation and stability of foams after in vitro digestive tests (with the corresponding exposure to gastric and intestinal juices, body temperature and mimicked peristaltic movements), and also in vivo studies. In in vitro studies, pH, overrun and drainage were determined with time. In in vivo, the foam stability was assessed by evaluating abdominal CT-scan images.

Concentration

Foams were prepared from dispersion containing disodium phosphate:monopotassium phosphate ($Na_2HPO_4$:$KH_2PO_4$) (75:25) buffers at 0.02, 0.04, 0.05 and 0.1 M. The latest made the intake of 1-1.5 L foam to be within the safe intake but close to the safe uptake of sodium, potassium and phosphate recommended by the pertinent authorities (i.e, WHO, EFSA, FDA). Due to the highest buffer capacity exhibited by 0.1 M, this buffer was the one chosen for foam preparation in order to face the harsh conditions along the gastrointestinal tract (mostly the significantly low pH in the stomach), and optimal pH (pH 7.3) to provide optimal conditions for egg white protein functionality and foam stability.

Several buffer concentrations were tested with $Na_2HPO_4$:$KH_2PO_4$ buffer (0.02, 0.04, 0.05, 0.1 M). Even though pH values remained stable after in vitro digestive treatments with foams with 0.02 and 0.04 M buffer concentration, both of them showed liquid drainage after standing at room temperature (23±1° C.) for 20 and 50 minutes, respectively. Foams prepared with buffer concentration at 0.1 M provided stable foams after digestion and standing at room temperature for at least 1 hour 5 minutes. However, 0.1 M gave too high saltiness in palatability, which led to an uncomfortable mouth feeling in most of the 25 volunteers under study in Example 1 during the foam intake and the saltiness mouth feeling could even last up to 1-3 hours. In addition to this, sodium (Na) and potassium (K) content in 1-1.5 L of foam with 0.1 M buffer concentration were within the safe intake levels and did not show any increase in serum levels after the intake, but the serum phosphate level showed a rise to an average of 1.7 mmol/L (mean value among 25 healthy volunteers) over the normal range (0.8-1.5 mmol/L). Even though the rise was not alarming (considering alarming to be twice the maximum value of the normal range), the phosphate serum levels should ideally remain within the normal range after the entire foam intake.

Foams prepared with buffer concentration 0.05 M (see further Examples 7-9) exhibited no liquid drainage for at least 1 hour 5 minutes. Likewise, it showed stable pH and stable foams in in vitro digestive tests with the corresponding chemical stress (presence of gastric juices at acid and neutral pH of the stomach and the small bowel, respectively) and physical stress (body temperature, 37° C., and mimicked peristaltic movements). The results for in vitro digestive tests were confirmed by in vivo trials and the corresponding evaluation of abdominal CT-scan images Furthermore, 0.05 M significantly decreased the saltiness in mouth feeling (nearly neutralized) and—although there are no proved evidences—it will also likely let the phosphate serum levels remain within the normal range since the concentration is reduced in half from 0.1 M.

Thus, 0.05 M buffer concentration showed not only optimal foam stability, and a safer intake due to the reduction in electrolyte levels, but also a palatability improvement by a notably decrease in saltiness.

Counter-Ion

The pH and degree of buffer capacity in the phosphate buffer is given by the ratio and concentration of the phosphate anionic specie, while the sodium and potassium are the cationic counter-ions than maintain the electric neutrality. Thus, once the optimal pH and buffer capacity have been found, the counter-ions can be modified for other purposes such reduction or suppression of saltiness in the product.

Thus, taking into account the saltiness index of Na (saltiness index, 1 as reference) and K (saltiness index, 0.6), $K_2HPO_4$:$NaH_2PO_4$ (75:25), 0.05 M phosphate buffer was tested as alternative to $Na_2HPO_4$:$KH_2PO_4$ (75:25), 0.05 M, and the results exhibited a completely neutralization of saltiness.

Hence, from the studies to obtain the optimal buffer it can be concluded that $K_2HPO_4$:$NaH_2PO_4$ (75:25), 0.05 M phosphate buffer provide the best conditions for obtaining not only stable foams with stable neutral pH, but also pleasant and palatable foams.

Apart from the differences mentioned above, all the foams with different buffer concentrations and counter-ions showed same foamability capability, appearance, bubble size, overrun, polydispersity, and consistency. All the foams reached the overrun under the same conditions, showed overrun around 130-140% (around 60% air content), bubble size around 70-80 μm, and consistency as 10.6 cm.

Example 3

Assessment of Type of EWP

Four different types of egg albumen powders (regular, high gel instant, super high gel instant, and high whip instant) were used for foam preparation under the same laboratory conditions and procedures in order to determine the EWP with the best foamability and foam stability properties. For statistics reasons and to confirm the reproducibility and the results obtained, three foams were prepared for each EWP-type.

EWP dispersions containing EWP (1 wt %) that was dispersed in phosphate buffer ($Na_2HPO_4$:$KH_2PO_4$ (75:25); 0.1 M; pH 7.3) and enzymatically treated with NPU protease. Xanthan gum (0.25 wt %) was added as stabilizer, as well as liquid flavoring (0.15-0.3 wt %). Flavoring was preferably 0.25-0.3 wt %.

The variations between experiments with the same EWP may be due to experimental errors (speed of powder addition, stirring/powder dispersion conditions, stirring time that it is stopped when complete dispersion is considered by bare eye) and external factors such as the degree of humidity in the atmosphere that may influence in the agglomeration of powder particles before its addition. The agglomeration hampers the powder dispersion, and it thus decreases the functionality of the components by the fact of not being entirely dispersed and incorporated in the system.

Super high gel exhibited higher tendency to agglomerate in powder state and thus longer times to be well-dispersed in solution. This may lead to a lower probability of success in complete powder dispersion. Regular, high gel instant, super high gel instant and high whip instant showed similar powder appearance, addition and dispersion procedure.

No differences were observed when using the different types of EWP. All the foams reached the aimed overrun at similar times applying the same whipping process, and all the foams showed same appearance when breaking up big bubbles to obtain homogenous foams. The four foams prepared with different type of EWP showed very similar foams in color, consistency and bubble size distribution right after whipping. Differences among them could not be discerned by the naked eye.

The main difference among the different EWP powders lays in the foam life-time (stability). Liquid drainage was evaluated with time and tests revealed increasing stability in the following order: super high gel (phase separation was observed after 35 minutes), high whip instant (phase separation was observed after 50 minutes), regular (phase separation was observed after 1 hour 10 minutes), and high gel instant (phase separation was observed after 1 hour 20 minutes). The stability was also assessed by determining the overrun with time, and it may be said that all foams showed the same stability tendency as for drainage. However, it was very difficult to determine average values and a clear tendency from three experiments. High gel instant (and regular in second position) seemed to show the lowest increasing values with time in overrun, and thus higher stability, but more experiments may be needed for better statistics and reliable concluded tendency.

From these experiments, it may be concluded that high gel instant EWP showed best foam stability results.

Example 4

Assessment of EWP Concentration and EWP:XG Ratio

Dispersions were prepared with increasing concentration of EWP (0.2, 0.5, 1, 2 and 3 wt %) with addition of xanthan gum (0.25, 0.375, 0.5, 0.625, 0.75 wt %) and whipped to obtain foams with 60% or 40% air content. The assessment of EWP concentration had to be combined with variations in XG concentration in order to evaluate the foam stability since the protein:stabilizer ratio also affects the stability as can be seen in Table 4 and in further Example 5.

TABLE 4

Effect of EWP concentration, XG concentration and air content in foam stability.

| EWP [%] | XG [%] | Air content [%] | Consistency [cm] | Stability | Notes |
|---|---|---|---|---|---|
| 0.2 | 0.25 | 60 | 11.8 | 0 min | Notably bigger bubbles and highly polydisperse |
| 0.5 | 0.25 | 60 | 9.9 | 35 min | Homogenous and low polydispersity. |
| 1 | 0.25 | 60 | 10.3 | 1 h 15 min | Homogenous and low polydispersity. |
| 2 | 0.25 | 60 | 10.2 | 50 min | Homogeneous and low polydispersity foams were obtained in significantly shorter time. |
| 1.5 | 0.375 | 40 | 9.6 | 50 min | Homogenous and low polydispersity foams were obtained in significantly shorter time. |
| 2 | 0.25 | 40 | 14.7 | 0 min | Homogeneous and low polydispersity foams were obtained in significantly shorter time. |
| 2 | 0.35 | 40 | 12 | 35 min | Homogeneous and low polydispersity foams were obtained in significantly shorter time. |
| 2 | 0.5 | 40 | 9.1 | 1 h 35 min | Homogeneous and low polydispersity foams were obtained in significantly shorter time. |
| 2.5 | 0.625 | 40 | 6.2 | 19 h | High polydispersity, big bubbles were clearly visible and differentiated. Too thick |

TABLE 4-continued

Effect of EWP concentration, XG concentration and air content in foam stability.

| EWP [%] | XG [%] | Air content [%] | Consistency [cm] | Stability | Notes |
|---|---|---|---|---|---|
| 3 | 0.5 | 40 | 7.3 | >19 h | High polydispersity, big bubbles were clearly visible and differentiated. Too thick |
| 3 | 0.75 | 40 | 6.1 | 19 h | High polydispersity, big bubbles were clearly visible and differentiated. Too thick. |

An increasing amount of EWP, in higher ratio than XG, showed better homogeneous foam formation and stability. The higher EWP concentration the smaller the bubbles formed during the first stage of incorporating air when whipping, and the easier to break them up during the second step during whipping to obtain a homogenous foam. Thus, homogeneous fluid foams with low polydispersity were easier and faster obtained when increasing EWP concentration provided XG concentration was lower than EWP concentration. When XG was added in higher ratio than EWP, the foams obtained showed significantly big bubbles when incorporating air, and those bubbles hampered and impeded the formation of a homogeneous foams due to the substantial difficulty in breaking them up.

Likewise, the higher concentration of EWP and XG, the higher foam stability. The more protein in the system, the more stabilizer is required to stabilize the gas bubbles dispersed in the continuous aqueous phase. From the experiments performed, EWP:XG (4:1) ratio was observed to be the optimal one for better foam stability. (More information about protein:stabilizer ratio can be found in Example 5).

A decrease in air content (from 60% to 40%) requires an increase in both EWP and its corresponding XG ratio (4:1). Thus, foam with EWP 1 wt % and XG 0.25 wt % and 60% air content showed similar stability than foam with EWP 2 wt % and 0.5 wt % with 40% air content. Both foams exhibited same fluid behavior despite the higher liquid content in foam with 40% air content due to the higher concentration of both surfactant and stabilizer, although the consistency was mostly influenced by the increase of XG concentration.

There is a notable improvement in both foamability and foam stability in dispersions containing EWP 2 wt % and XG 0.5 wt %. A fluid and homogeneous foam with small bubbles size could be quickly obtained (even after 2.5 minutes whipping) and remained stable for 2 h 45 min in open beaker slightly covered with aluminum foil.

However, when the EWP concentration was increased to 2.5 and 3 wt % with its corresponding addition of XG (0.625 and 0.75 wt %, respectively (EWP:XG, 4:1), there was a clear difficulty in obtaining a low polydisperse and homogenous foam during whipping. Big bubbles were created at the surface and in the bulk, which could not be broken up after 5 minutes whipping. Moreover, the consistency significantly decreased making hard to drink up even just one dose (300 mL).

Example 5

Assessment of Stabilizer (Xanthan Gum) Concentration

Increasing amount of Xanthan gum (0, 0.15, 0.20, 0.25, 0.31 wt %) was added to high gel instant EWP to assess the optimal amount to obtain a stable fluid foam. The foams were prepared under the same conditions and procedure in order to study and determine the optimal amount of stabilizer. Every test was performed twice to confirm the reproducibility and the results obtained.

EWP dispersion contained EWP (1 wt %) that was dispersed in phosphate buffer ($Na_2HPO_4$:$KH_2PO_4$ (75:25), 0.1 M, pH 7.3) and enzymatically treated with NPU protease. Xanthan gum was added as stabilizer, as well as liquid flavoring (0.15-0.3 wt %).

All the foams were prepared following the same procedure and formula except for the concentration of xanthan gum.

Dispersions containing xanthan gum (0, 0.15 wt %) showed significantly lower foamability by exhibiting longer time requirements to reach the aimed overrun (air content). The dispersions and foams formed were observed to be notably less viscous—too close to water-like—than foams containing higher xanthan gum concentration, the lower viscosity lead to difficulties in keeping the blender stable— and the blender was particularly shaky—. Dispersions containing 0.20, 0.25 wt % showed very similar foamability capability and very similar foam appearance, as well as very similar values in bubble size and overrun. In contrary, dispersions containing 0.31 wt % exhibited a clearly more viscous dispersion and stiffer foam from the starting point of whipping process. Too big bubbles were formed and impediments were found to obtain a homogenous foam when trying to break them up. Actually, the final foam showed notable higher polydispersity that could directly be observed by bare eye. Thus, 0.31 wt % hampered and impeded the formation of homogeneous fluid foam.

Foams containing 0, 0.15, 0.20 and 0.25 wt % of XG and air content around 60% led to fluid foams with bubble size around –70-80 μm. However, foam containing XG 0.31 wt % and 40% air showed notably thicker (spoonable, despite the higher liquid content) and polydisperse foam.

Foams containing xanthan gum (0, 0.15, 0.20, 0.31 wt %) showed clear instability since liquid phase was observed right after the foam formation in dispersions containing 0, 0.15, 0.31 wt %, while 15 minutes after foam formation when xanthan gum was added in 0.20 wt %, respectively. A clear onset was observed for xanthan gum 0.25 wt %, which allows obtaining a homogeneous fluid foam that was stable for an average of 1 hour 15 minutes.

From these experiments, it could be concluded that 0.25 wt % xanthan gum is the optimal amount that provided optimal foamability capability, foam stability, and appearance (homogenous and low polydisperse fluid foam with bubble size around –70-80 μm) in foams containing 60% air.

Example 6

Assessment of Whipping Conditions

Speed

Dispersions containing high instant gel EWP (1 wt %) and XG (0.25 wt %) in $K_2HPO_4$:$NaH_2PO_4$ phosphate buffer (75:25), 0.05 M (without hydrolytic enzymatic treatment) were whipped using a blender Bamix®Gastro 350 equipped with a flat blade, under 18 000 rpm and 23 000 rpm to study the influence of the mechanical force applied to the system. All the foams were characterized with time by determining the evolution of overrun and detection of drainage by bare eye while exposing the foam to white natural bulb (and tilting the beaker) in order to avoid neglecting any possible liquid phase present at the bottom.

No differences were observed in neither foamability, nor foam stability, nor bubble size, nor polydispersity, nor consistency of foams formed under different blade speed.

Temperature

Foams containing high gel instant EWP (1 wt %) and XG (0.25 wt %), and flavoring (0.3 wt %) in $K_2HPO_4:NaH_2PO_4$ (75:25), 0.05 M phosphate buffer were prepared to assess the influence of temperature of the dispersion during the whipping process in foamability and stability. Two dispersions were prepared and stored in the fridge for 2-3 hours to cool the dispersion down to around 9° C. Then, the dispersions were placed in an ice-water bath to keep them chilled and whipped for nearly 5 minutes under 18 000 rpm. In parallel, two dispersions were prepared, slightly cooled down to around 20° C., and whipped at room temperature for almost 5 minutes under 18 000 rpm. And likewise, dispersions at 23° C. were whipped at room temperature for almost 5 minutes under 18 000 rpm.

All the foams showed very similar and good foamability properties. All the dispersions required the same whipping time to reach the aimed air content. All the big bubbles formed during the first stage during the whipping process could be easily broken up to provide homogeneous and low polydisperse fluid foams with similar values for overrun (between 120-140%) or air content (around 60%), for bubble size (around ~70-80 μm), and evolution of these two parameters with time. Likewise, the consistency was determined as 10.3 cm, which is notably similar to the consistency for foams obtained at room temperature (10.6 cm).

Foam stability was evaluated by liquid drainage assessment every 5, 10, 15 or 20 minutes for 2 hours. Liquid drainage started to be detected at the bottom of all the foams 1 hour 5 minutes after their preparation. Hence, it could be concluded that the dispersion temperature has no influence in neither foamability nor foam stability.

Example 7

Formulation 2

Foams were prepared with food-grade ingredients, phosphate buffer $K_2HPO_4:NaH_2PO_4$ ((75:25), 0.05 M, pH 7.3), EWP (1 wt %), XG (0.25 wt %), flavor (0.1-0.3 wt %).

EWP in formulation 2, and further formulations 3 and 4 (cf. below), was not enzymatically treated with NPU since the foams showed the same behavior and properties without proteolytic treatment.

The edible negative contrast agent showed the following characterization:
Overrun: Around 140% (around 60% air content)
Bubble size: d=70-80 μm
pH 7.3 (22° C.)
Consistency: 10.6 cm
Palatability: Acceptable to drink and neutral flavor.
Stability: Foams showed life-time (no liquid drainage at all and constant total foam volume) for approximately 1 h 15 min in glass beaker covered with aluminium foil, which is longer time than the total time (around 50 minutes) that was observed to be required for both the foam intake and the CT-abd examination (around a total of 60 minutes, see Example 1, in vivo test).

Feasibility in In Vitro Digestive Test:

The characterization of the foam was performed after gastric and intestinal digestive treatment. The foam was exposed to body temperature (37° C.), mechanical stress, and digestive enzymes. The foam showed an increase in overrun of around 20%. The pH remained stable (pH 7.3). Liquid drainage was observed, most of it likely corresponded to the 9.5 mL of gastrointestinal juices added during the digestive treatment, thus only 1.3% of the total foam volume was liquid that drained from the continuous aqueous phase of the foam. It is worth to mention that the in vitro test was performed for a total of 2 hours (time for digestion of solid food) instead of 1 hour (time for digestion of liquid food). Moreover, the volume of gastrointestinal fluid is expected to be notably lower than the added for two reasons: a) the subject will be in fasted state, b) it is to be presumed that the composition of high air and low amount of egg protein will induce only a minimal mucosal stimulation to produce gastro-intestinal juices.

Example 8

Formulation 3

Foams were prepared with food-based ingredients, phosphate buffer $K_2HPO_4:NaH_2PO_4$ ((75:25), 0.05 M, pH 7.3), EWP (2 wt %), XG (0.5 wt %), flavor (0.1-0.3 wt %).

EWP in Formulation 3 was not enzymatically treated with NPU, like in Formulation 2 and 4.

The edible negative contrast agent showed the following characterization:
Overrun: 70-100%
Air content: 43-50%
Bubble size: d=70-120 μm
pH 7.3 (22° C.)
Consistency: 7.4-9.3 cm
Dry matter: 2.9%
Palatability: Easy to drink and neutral flavor.
Stability: Foams showed life-time (no liquid drainage at all and constant total volume) for 7 hours in a glass beaker slightly covered with aluminium foil. No liquid phase was detected for at least 26 hours in a well-closed glass bottle filled up with foam, although an increase in bubble size was observed.

Feasibility in In Vitro Digestive Test

The characterization of the foam was performed after simulated gastric and intestinal digestive treatment. The foam was exposed to body temperature (37° C.), mechanical stress, and digestive enzymes. The foam was incubated with gastric and intestinal digestive enzymes for 30 minutes at each stage since the fluid foam was observed to reach the large bowel in less than 1 hour during the in vivo tests (with Formulation 1) with healthy volunteers. The foam showed an increase in overrun around 0-5% (which are values within the experimental error), a constant total foam volume (100 mL) in 100 mL glass cylinders, and stable pH (pH 7.3). Liquid drainage was observed at the bottom of the beakers, but the volume was even less than the volume of the added gastrointestinal juices (9.5 mL) that might partially remain incorporated in the continuous aqueous phase, and which may be mixed and homogenized in the gut by the peristaltic movements. Moreover, the volume of gastrointestinal fluid in vivo is expected to be notably lower than the added during the in vitro test for two reasons: a) the subject will be in fasted state, b) it is to be presumed that the composition of high air and low amount of egg protein will induce only a minimal mucosal stimulation to produce gastro-intestinal juices.

CT-Imaging 1.25 mm thick slices of CT-images were primarily presented in transverse direction. Sagittal and coronal images were reconstructed from the axial ones. The default presentation of images is set in an abdominal window. Inverted image presentation and lung window presentation are options for the diagnostic work-up.

CT-scan images obtained in both abdominal (ordinary diagnostic grey scale for CT-abd) and lung windows (bright grey scale for reading CT of the lungs) showed that the foams were stable and homogenously distributed along the tubes. Even though the mean bubble size increased with time and after digestion, no interferences from isolated and disproportionate big bubbles due to foam instability were detected. Moreover, the contrast density of negative HU was measured at different points in coronal and transversal sections and gave a mean value of approximately minus 400.

Feasibility in In Vivo Test (Clinical Trial)

Three healthy volunteers took around 900 mL of foam Formulation 3 since 900 mL was observed to be enough to fill up the small bowel. The procedure followed was the same for the in vivo test under Clinical Trial for Formulation 1.

Figure 3A:
In FIG. 3a the abdominal window being the window used for diagnosis and exhibiting the lumen of the gut in dark is depicted; and in FIG. 3b an inverted image showing the negative contrast agent in white is depicted.
Figure 3B:
FIG. 3 Depicts images obtained from abdominal CT-scan examinations in a healthy subject by use of the present contrast agent according to another embodiment having a density contrast around minus 400 HU.

The CT-scan images (FIG. 3) showed good and homogenous distribution, almost continuous in the small bowel. Table 5 shows the contrast density [HU] values obtained at different sections in the gastrointestinal tract.

The three volunteers considered the foam to be very easy to drink and swallow (preferred over formulation 1 and 2), the texture and taste to be smooth and well accepted. No side effects were reported.

TABLE 5

Contrast density obtained in different sections of the gastrointestinal tract filled with foam from Formulation 3.

| Section | Contrast density [HU] | Standard deviation |
| --- | --- | --- |
| Stomach | −408 | 25 |
| Duodenum | ND | ND |
| Jejunum | −428 | 24 |
| Proximal ileum | −444 | 30 |
| Middle ileum | −420 | 11 |
| Distal Ileum | −355 | 45 |
| Terminal ileum | −399 | 89 |
| Caecum | ND | ND |

Example 9

Formulation 4

Foams were prepared with ingredients included in the European Pharmacopeia (Ph. Eur.), phosphate buffer $K_2HPO_4:NaH_2PO_4$ ((75:25), 0.05 M, pH 7.3), EWP (2 wt %), XG (0.5 wt %), flavor (0.1-0.3 wt %).

EWP in Formulation 4 was not enzymatically treated with NPU, like in Formulation 2 and 3.

The only difference between Formulation 3 and 4 is the supplier and application of the ingredients, being food-grade the ones used for Formulation 3, while included in the Ph. Eur. the ones used for Formulation 4.

The edible negative contrast agent showed the following characterization:
Overrun: 75-115%
Air content: 43-50%
Bubble size: d=100-140 μm
pH 7.3 (22° C.)
Consistency: 7.5-8.6 cm
Palatability: Easy to drink and neutral flavor.
Stability: Foams showed life-time (no liquid drainage at all and constant total volume) for at least 7 hours in an opened jar.

The dispersion stability was also evaluated by microbiological analysis on dispersions stored in well-closed PET containers where argon replaced the air between the top of the dispersion and the lid of the container, and under controlled temperature between 5±3° C. Microbiological analysis were periodically performed for total aerobic microbial count (TAMC), total yeast/mold count (TYMC), *Salmonella, Escherichia coli*, and Bile-tolerant gram-negative bacteria. The dispersion for Formulation 3 showed stability for at least 3 months as shown in Table 6.

TABLE 6

Microbiological analysis results for dispersion stored at 5 ± 3° C. in well-closed containers filled with argon.

| Microbiological analysis | Maximum limit | Results | | | | | |
| --- | --- | --- | --- | --- | --- | --- | --- |
| | | Day 0 | 2 weeks | 1 month | 1.5 months | 2 months | 3 months |
| TAMC | $10^4$ CFU/g | <100 | <100 | <100 | <100 | <100 | <100 |
| TYMC | $10^2$ CFU/g | <10 | <10 | <10 | <10 | <10 | <10 |
| Salmonella | Absent | Absent | Absent | Absent | Absent | Absent | Absent |
| *Escherichia Coli* | Absent | Absent | Absent | Absent | Absent | Absent | Absent |

The foams obtained with Formulation 4, which contains ingredients included in the Ph. Eur., showed same appearance and properties than foams from Formulation 3 during both the production and characterization. Moreover, microbiological analysis performed to dispersions prepared with Formulation 4, that were stored under argon and chilled (5±3° C.), indicated a safe shelf-life for at least 3 months. Thus, the foams obtained from Formulation 4 gave indication of suitable use of the product for medical applications in hospitals.

Additionally, foam results from Formulation 4 confirmed the high degree of reproducibility of both the product production and characterization that showed all the parameters (overrun, air content, bubble size, pH, consistency, palatability, stability) to be within the limited range for good result in the aimed application of the foam.

The invention claimed is:

1. A method of CT imaging the gastrointestinal tract, including at least the upper part of the small intestine, of a subject, the method comprising:
   a) prior to the CT imaging, orally administering to the subject to be examined an edible negative contrast agent for CT imaging of the gastrointestinal tract intended for oral intake, the contrast agent being a fluid, aqueous foam displaying a CT density contrast value in the range −300 to −800 HU, wherein the contrast agent comprises an aqueous continuous liquid phase having a pH of 6.5 to 8.0, the aqueous continuous liquid phase comprising:
      0.1 to 5 wt % of a surfactant, the surfactant being a protein;
      0.01 to 1.0 wt % of a hydrocolloid acting as foam stabilizer;
      a buffering agent; and
      water;
      and gas bubbles dispersed in the continuous aqueous liquid phase, the contrast agent having a consistency of 7 to 12 cm as measured with Bostwick consistometer over 30 seconds at 23±1° C., wherein the weight ratio surfactant hydrocolloid in the continuous liquid phase is from 8:1 to 2:1; and
   b) using a computerized tomography to obtain a CT image of the subject's abdomen.

2. The method according to claim 1, wherein the gas bubbles dispersed in the continuous aqueous liquid phase are air bubbles.

3. The method according to claim 1, wherein the surfactant comprises ovalbumin.

4. The method according to claim 1, wherein the contrast agent comprises at least 35 vol % dispersed air bubbles.

5. The method according to claim 4, wherein the contrast agent comprises 35 to 55 vol % dispersed air bubbles at 25° C.

6. The method according to claim 1, wherein the contrast agent displays a density contrast value in the range −500 to −700 HU.

7. The method according to claim 1, wherein the contrast agent has a consistency of 8.5 to 12.0 cm as measured with Bostwick consistometer over 30 seconds at 23±1° C.

8. The method according to claim 1, wherein the weight ratio surfactant:hydrocolloid in the continuous liquid phase is from 3:1 to 5:1.

9. The method according to claim 1, wherein the hydrocolloid is:
   a polysaccharide;
   a natural gum;
   chitosan; or
   a modified natural gum.

10. The method according to claim 9, wherein the hydrocolloid is a natural gum or a modified natural gum.

11. The method according to claim 1, wherein the buffering agent comprises a counter-ion, the counter-ion being monovalent.

12. The method according to claim 11, wherein the buffering agent is phosphate based and the counter-ions are sodium and potassium, the phosphate concentration in the liquid phase being between 0.01 and 1 molar.

13. The method according to claim 1, wherein:
   the content of dry matter in the continuous aqueous liquid phase is 5 wt % or less; and/or
   the continuous aqueous liquid phase comprises 0.1 to 0.7 wt % of the hydrocolloid; and/or
   the continuous aqueous liquid phase comprises 0.5 to 2.5 wt % of the surfactant; and/or
   the negative contrast agent displays a CT density in the range −300 to −700 HU.

14. The method according to claim 1, wherein the method further comprises the step of foaming an aqueous liquid composition to provide the fluid, aqueous foam, wherein the aqueous liquid composition comprises:
   0.1 to 5 wt % of a surfactant, the surfactant being a protein;
   0.01 to 1.0 wt % of a hydrocolloid acting as foam stabilizer;
   a buffering agent; and
   water;
   and wherein the weight ratio surfactant:hydrocolloid in the aqueous liquid composition is from 8:1 to 2:1.

15. The method according to claim 14, wherein the method further comprises the step of dispersing a dry composition in water to provide the aqueous liquid composition, and wherein the dry composition comprises:
   a surfactant, the surfactant being egg albumen;
   a hydrocolloid; and
   a buffering agent;
   the weight ratio surfactant:hydrocolloid being from 8:1 to 2:1.

16. The method according to claim 4, wherein the contrast agent comprises 55 to 65 vol % dispersed air bubbles at 25° C.

17. The method according to claim 9, wherein the hydrocolloid is xanthan gum or propylene glycol alginate.

* * * * *

UNITED STATES PATENT AND TRADEMARK OFFICE
CERTIFICATE OF CORRECTION

PATENT NO.        : 11,179,483 B2
APPLICATION NO.   : 16/489063
DATED             : November 23, 2021
INVENTOR(S)       : Lucia Casal-Dujat et al.

Page 1 of 1

It is certified that error appears in the above-identified patent and that said Letters Patent is hereby corrected as shown below:

On the Title Page

Item [73], delete "LUMENTAB" and insert --LUMENT AB--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*